United States Patent
Yang et al.

(10) Patent No.: US 10,675,118 B2
(45) Date of Patent: Jun. 9, 2020

(54) APPARATUS AND METHOD FOR DELIVERY OF CONCENTRATED DISINFECTANT OR STERILANT TO LUMEN OF MEDICAL INSTRUMENT

(71) Applicant: ASP Global Manufacturing GmbH, Schaffhausen (CH)

(72) Inventors: Sungwook Yang, Tustin, CA (US); Navid Omidbakhsh, Mission Viejo, CA (US)

(73) Assignee: ASP GLOBAL MANUFACTURING GMBH, Schaffhausen (CH)

(*) Notice: Subject to any disclaimer, the term of this patent is extended or adjusted under 35 U.S.C. 154(b) by 0 days.

(21) Appl. No.: 15/696,420

(22) Filed: Sep. 6, 2017

(65) Prior Publication Data

US 2019/0069972 A1 Mar. 7, 2019

(51) Int. Cl.
*A61B 1/12* (2006.01)
*A61B 90/70* (2016.01)
(Continued)

(52) U.S. Cl.
CPC .............. *A61B 90/70* (2016.02); *A61B 1/123* (2013.01); *A61B 1/125* (2013.01); *B08B 7/0071* (2013.01);
(Continued)

(58) Field of Classification Search
CPC ......... A61B 1/123; A61B 1/125; A61B 90/70; A61B 2090/701; B08B 7/0071;
(Continued)

(56) References Cited

U.S. PATENT DOCUMENTS

| 6,986,736 B2 | 1/2006 | Williams et al. |
| 7,479,257 B2 | 1/2009 | Nguyen et al. |
| (Continued) | | |

FOREIGN PATENT DOCUMENTS

| EP | 0 549 674 A1 | 7/1993 |
| EP | 0 549 674 B1 | 11/1996 |
| (Continued) | | |

OTHER PUBLICATIONS

U.S. Appl. No. 15/157,800, filed May 18, 2016.
(Continued)

*Primary Examiner* — Levon J Shahinian
(74) *Attorney, Agent, or Firm* — Frost Brown Todd LLC

(57) ABSTRACT

A medical device processor includes an enclosure for holding at least one medical device, a first reservoir containing a disinfectant therein, a water source containing water therein and in fluid communication with a mixing chamber, and a liquid distribution system configured to deliver disinfectant from the first reservoir to the at least one medical device. The liquid distribution system is configured to deliver water from the water source to the mixing chamber. The liquid distribution system includes a pump and a flow sensor. The pump is operable to deliver the disinfectant from the first reservoir to an internal channel of the at least one medical device. The flow sensor is operable to monitor the disinfectant delivered by the pump to the internal channels of the at least one medical device.

14 Claims, 12 Drawing Sheets

(51) Int. Cl.
*B08B 7/00* (2006.01)
*B08B 9/023* (2006.01)
*B08B 9/027* (2006.01)
*B08B 9/032* (2006.01)

(52) U.S. Cl.
CPC .............. *B08B 9/023* (2013.01); *B08B 9/027* (2013.01); *B08B 9/0323* (2013.01); *B08B 9/0325* (2013.01); *A61B 2090/701* (2016.02)

(58) Field of Classification Search
CPC ....... B08B 9/023; B08B 9/027; B08B 9/0323; B08B 9/0325
USPC .............. 134/22.13, 22.16, 22.19, 94.1, 109, 134/166 R, 184
See application file for complete search history.

(56) References Cited

U.S. PATENT DOCUMENTS

| | | |
|---|---|---|
| 7,686,761 B2 | 3/2010 | Jackson et al. |
| 8,246,909 B2 | 8/2012 | Williams et al. |
| 2009/0060798 A1* | 3/2009 | Williams ................. A61L 2/18 422/111 |

FOREIGN PATENT DOCUMENTS

| | | |
|---|---|---|
| EP | 1 025 795 A1 | 8/2000 |
| EP | 2 462 861 A1 | 6/2012 |
| JP | H06-38927 A | 2/1994 |

OTHER PUBLICATIONS

U.S. Appl. No. 15/157,952, filed May 18, 2016.
European Search Report, Extended, and Written Opinion dated Nov. 30, 2018 for Application No. EP 18192635.3, 8 pgs.

* cited by examiner

APPARATUS AND METHOD FOR DELIVERY OF CONCENTRATED DISINFECTANT OR STERILANT TO LUMEN OF MEDICAL INSTRUMENT

BACKGROUND

The below discussion relates to the reprocessing (i.e., decontamination) of endoscopes and other instruments that are used in medical procedures. In particular, the below discussion relates to an apparatus and a method that may be used to reprocess a medical device such as an endoscope after the medical device has been used in a first medical procedure, such that the medical device may be safely used in a subsequent medical procedure. While the below discussion will speak mainly in terms of an endoscope, it should be understood that the discussion may also equally apply to certain other medical devices.

An endoscope may have one or more working channels or lumens extending along at least a portion of the length of the endoscope. Such channels may be configured to provide a pathway for passage of other medical devices, etc., into an anatomical region within a patient. These channels may be difficult to clean and/or disinfect using certain primitive cleaning and/or disinfecting techniques. Thus, the endoscope may be placed in a reprocessing system that is particularly configured to clean endoscopes, including the channels within endoscopes. Such an endoscope reprocessing system may wash and disinfect the endoscope. Such an endoscope reprocessing system may include a basin that is configured to receive the endoscope, with a pump that flows cleaning fluids over the exterior of the endoscope within the basin. The system may also include ports that couple with the working channels of the endoscope and associated pumps that flow cleaning fluids through the working channels of the endoscope. The process executed by such a dedicated endoscope reprocessing system may include a detergent washing cycle, followed by a rinsing cycle, followed by a sterilization or disinfection cycle, followed by another rinsing cycle. The sterilization or disinfection cycle may employ disinfectant solution and water rinses. The process may optionally include an alcohol flush to aid displacement of water. A rinsing cycle may be followed by an air flush for drying and storage.

Examples of systems and methods that may be used to reprocess a used endoscope are described in U.S. Pat. No. 6,986,736, entitled "Automated Endoscope Reprocessor Connection with Integrity Testing," issued Jan. 17, 2006, the disclosure of which is incorporated by reference herein; U.S. Pat. No. 7,479,257, entitled "Automated Endoscope Reprocessor Solution Testing," issued Jan. 20, 2009, the disclosure of which is incorporated by reference herein; U.S. Pat. No. 7,686,761, entitled "Method of Detecting Proper Connection of an Endoscope to an Endoscope Reprocessor," issued Mar. 30, 2010, the disclosure of which is incorporated by reference herein; and U.S. Pat. No. 8,246,909, entitled "Automated Endoscope Reprocessor Germicide Concentration Monitoring System and Method," issued Aug. 21, 2012, the disclosure of which is incorporated by reference herein. An example of a commercially available endoscope reprocessing system is the EVOTECH® Endoscope Cleaner and Reprocessor (ECR) by Advanced Sterilization Products of Irvine, Calif.

Some versions of reprocessing systems may provide just a single use of a certain volume of disinfectant solution, such that the used volume of disinfectant solution is disposed of after a single rise of the volume of disinfectant solution upon completion of the disinfection cycle. In some such versions, the system may check the concentration of the in-use disinfectant solution to confirm that the concentration level is sufficient at the beginning of (or prior to commencing) a disinfection cycle. Some other versions of reprocessing system may check the concentration level of a used volume of disinfectant solution and either re-use the used disinfectant solution (i.e., if the concentration level is still acceptable) or dispose of the used disinfectant solution (i.e., if the concentration level is no longer acceptable). Examples of versions of reprocessing systems that provide monitoring and re-use of disinfectant solution are disclosed in U.S. Pat. No. 8,246,909, entitled "Automated Endoscope Reprocessor Germicide Concentration Monitoring System and Method," issued Aug. 21, 2012, the disclosure of which is incorporated by reference herein; in U.S. patent application Ser. No. 15/157,800, entitled "Apparatus and Method for Reprocessing a Medical Device," filed on May 18, 2016, the disclosure of which is incorporated by reference herein; and in in U.S. patent application Ser. No. 15/157,952, entitled "Apparatus and Method to Measure Concentration of Disinfectant in Medical Device Reprocessing system," filed on May 18, 2016, the disclosure of which is incorporated by reference herein.

While a variety of systems and methods have been made and used to reprocess medical devices, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
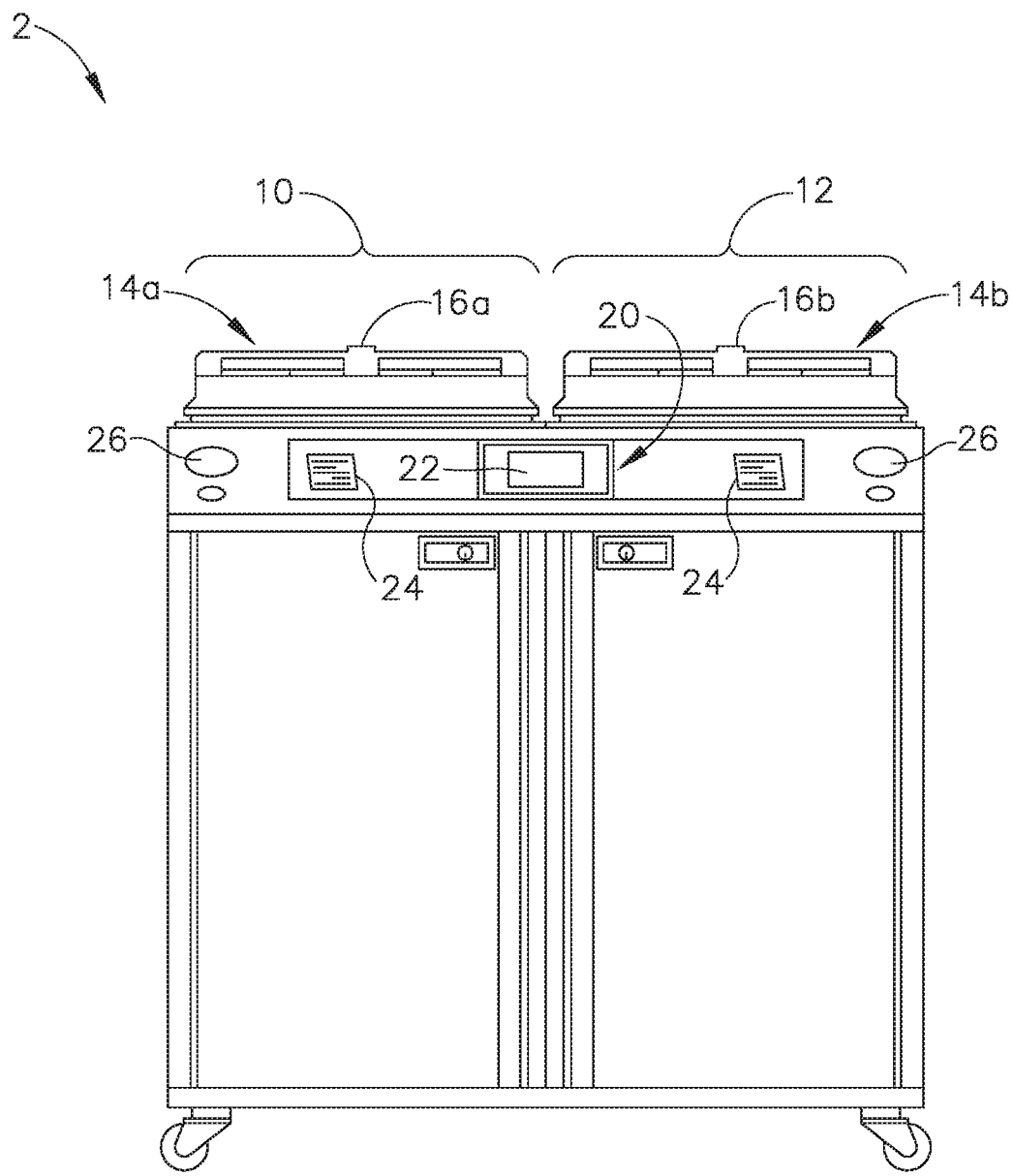
FIG. 1 depicts a front elevational view of an exemplary reprocessing system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Figure 2:
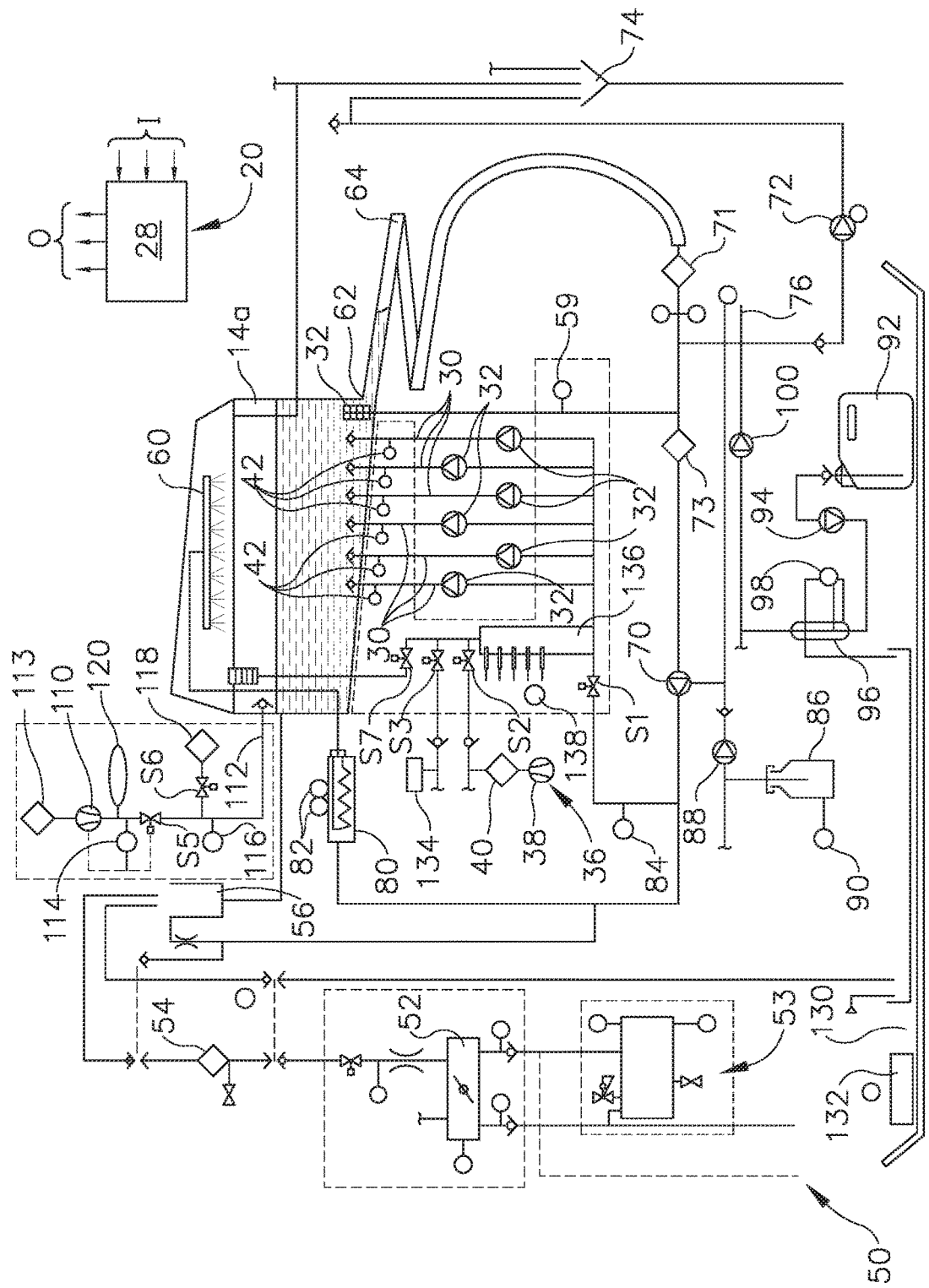
FIG. 2 depicts a schematic diagram of the reprocessing system of FIG. 1, with only a single decontamination basin shown for clarity.

I. Exemplary Medical Device Reprocessing Apparatus with Single-Use Disinfectant FIGS. 1-2 show an exemplary reprocessing system (2) that may be used to decontaminate endoscopes and other medical devices that include channels or lumens formed therethrough. System (2) of this example generally includes a first station (10) and a second station (12). Stations (10, 12) are at least substantially similar in all respects to provide for the decontamination of two different medical devices simultaneously or in series. First and second decontamination basins (14a, 14b) receive the contaminated devices. Each basin (14a, 14b) is selectively sealed by a respective lid (16a, 16b). In the present example, lids (16a, 16b) cooperate with respective basins (14a, 14b) to provide a microbe-blocking relationship to prevent the entrance of environmental microbes into basins (14a, 14b) during decontamination operations. By way of example only, lids (16a, 16b) may include a microbe removal or HEPA air filter formed therein for venting.

A control system (20) includes one or more microcontrollers, such as a programmable logic controller (PLC), for controlling decontamination and user interface operations. Although one control system (20) is shown herein as controlling both decontamination stations (10, 12), those skilled in the art will recognize that each station (10, 12) can include a dedicated control system. A visual display (22) displays decontamination parameters and machine conditions for an operator, and at least one printer (24) prints a hard copy output of the decontamination parameters for a record to be filed or attached to the decontaminated device or its storage packaging. It should be understood that printer (24) is merely optional. In some versions, visual display (22) is combined with a touch screen input device. In addition, or in the alternative, a keypad and/or other user input feature is provided for input of decontamination process parameters and for machine control. Other visual gauges (26) such as pressure meters and the like provide digital or analog output of decontamination or medical device leak testing data.

FIG. 2 diagrammatically illustrates just one decontamination station (10) of reprocessing system (2), but those skilled in the art will recognize that decontamination station (12) may be configured and operable just like decontamination station (10). It should also be understood that reprocessing system (2) may be provided with just one single decontamination station (10, 12) or more than two decontamination stations (10, 12).

Decontamination basin (14a) receives an endoscope (200) (see FIG. 3) or other medical device therein for decontamination. Any internal channels of endoscope (200) are connected with flush conduits, such as flush lines (30). Each flush line (30) is connected to an outlet of a corresponding pump (32), such that each flush line (30) has a dedicated pump (32) in this example. Pumps (32) of the present example comprise peristaltic pumps that pump fluid, such as liquid and air, through the flush lines (30) and any internal channels of endoscope (200). Alternatively, any other suitable kind of pump(s) may be used. In the present example, pumps (32) can either draw liquid from basin (14a) through a filtered drain and a valve (S1); or draw decontaminated air from an air supply system (36) through a valve (S2). Air supply system (36) of the present example includes a pump (38) and a microbe removal air filter (40) that filters microbes from an incoming air stream.

A pressure switch or sensor (42) is in fluid communication with each flush line (30) for sensing excessive pressure in the flush line. Any excessive pressure or lack of flow sensed may be indicative of a partial or complete blockage (e.g., by bodily tissue or dried bodily fluids) in an endoscope (200) channel to which the relevant flush line (30) is connected. The isolation of each flush line (30) relative to the other flush lines (30) allows the particular blocked channel to be easily identified and isolated, depending upon which sensor (42) senses excessive pressure or lack of flow.

Basin (14a) is in fluid communication with a water source (50), such as a utility or tap water connection including hot and cold inlets, and a mixing valve (52) flowing into a break tank (56). A microbe removal filter (54), such as a 0.2 μm or smaller absolute pore size filter, decontaminates the incoming water, which is delivered into break tank (56) through the air gap to prevent backflow. A sensor (59) monitors liquid levels within basin (14a). An optional water heater (53) can be provided if an appropriate source of hot water is not available. The condition of filter (54) can be monitored by directly monitoring the flow rate of water therethrough or indirectly by monitoring the basin fill time using a float switch or the like. When the flow rate drops below a select threshold, this indicates a partially clogged filter element that requires replacement.

A basin drain (62) drains liquid from basin (14a) through an enlarged helical tube (64) into which elongated portions of endoscope (200) can be inserted. Drain (62) is in fluid communication with a recirculation pump (70) and a drain pump (72). Recirculation pump (70) recirculates liquid from basin drain (62) to a spray nozzle assembly (60), which sprays the liquid into basin (14a) and onto endoscope (200). A coarse screen (71) and a fine screen (73) filter out particles in the recirculating fluid. Drain pump (72) pumps liquid from basin drain (62) to a utility drain (74). A level sensor (76) monitors the flow of liquid from pump (72) to utility drain (74). Pumps (70, 72) can be simultaneously operated such that liquid is sprayed into basin (14a) while basin (14a) is being drained, to encourage the flow of residue out of basin (14a) and off of endoscope (200). Of course, a single pump and a valve assembly could replace dual pumps (70, 72).

An inline heater (80) with temperature sensors (82), upstream of recirculation pump (70), heats the liquid to optimum temperatures for cleaning and/or disinfection. A pressure switch or sensor (84) measures pressure downstream of circulation pump (70). In some variations, a flow sensor is used instead of pressure sensor (84), to measure fluid flow downstream of circulation pump (70). Detergent solution (86) is metered into the flow downstream of circulation pump (70) via a metering pump (88). A float switch (90) indicates the level of detergent (86) available. Disinfectant (92) is metered into the flow upstream of circulation pump (70) via a metering pump (94). To more accurately meter disinfectant (92), pump (94) fills a metering prechamber (96) under control of a fluid level switch (98) and control system (20). By way of example only, disinfectant solution (92) may comprise an activated glutaraldehyde solution such as CIDEX® Activated Glutaraldehyde Solution by Advanced Sterilization Products of Irvine, Calif. By way of further example only, disinfectant solution (92) may comprise ortho-phthalaldehyde (OPA), such as CIDER® ortho-phthalaldehyde solution by Advanced. Sterilization Products of Irvine, Calif. By way of further example only, disinfectant solution (92) may comprise peracetic acid (PAA), hydrogen peroxide, and/or any other chemical composition capable of achieving disinfection.

Some endoscopes (200) include a flexible outer housing or sheath surrounding the individual tubular members and the like that form the interior channels and other parts of endoscope (200). This housing defines a closed interior space, which is isolated from patient tissues and fluids during medical procedures. It may be important that the sheath be maintained intact, without cuts or other holes that would allow contamination of the interior space beneath the sheath. Therefore, reprocessing system (2) of the present example includes means for testing the integrity of such a sheath. In particular, an air pump (e.g., pump (38) or another pump (110)) pressurizes the interior space defined by the sheath of endoscope (200) through a conduit (112) and a valve (S5). In the present example, a HEPA or other microbe-removing filter (113) removes microbes from the pressurizing air. A pressure regulator (114) prevents accidental over pressurization of the sheath. Upon full pressurization, valve (S5) is closed and a pressure sensor (116) looks for a drop in pressure in conduit (112), which would indicate the escape of air through the sheath of endoscope (200). A valve (S6) selectively vents conduit (112) and the sheath of endoscope (200) through an optional filter (118) when the testing procedure is complete. An air buffer (120) smoothes out pulsation of pressure from air pump (110).

In the present example, each station (10, 12) also contains a drip basin (110) and spill sensor (132) to alert the operator to potential leaks.

An alcohol supply (134), controlled by a valve (S3), can supply alcohol to channel pumps (32) after rinsing steps, to assist in removing water from channels (210, 212, 213, 214, 217, 218) of endoscope (200).

Flow rates in lines (30) can be monitored via channel pumps (32) and pressure sensors (42). If one of pressure sensors (42) detects too high a pressure, the associated pump (32) is deactivated. The flow rate of pump (32) and its activated duration time provide a reasonable indication of the flow rate in an associated line (30). These flow rates are monitored during the process to check for blockages in any of the channels of endoscope (200). Alternatively, the decay in the pressure from the time pump (32) cycles off can also be used to estimate the flow rate, with faster decay rates being associated with higher flow rates.

A more accurate measurement of flow rate in an individual channel may be desirable to detect subtler blockages. To that end, a metering tube (136) having a plurality of level indicating sensors (138) fluidly connects to the inputs of channel pumps (32). In some versions, a reference connection is provided at a low point in metering tube (136) and a plurality of sensors (138) are arranged vertically above the reference connection. By passing a current from the reference point through the fluid to sensors (138), it can be determined which sensors (138) are immersed and therefore determine the level within metering tube (136). In addition, or in the alternative, any other suitable components and techniques may be used to sense fluid levels. By shutting valve (S1) and opening a vent valve (S7), channel pumps (32) draw exclusively from metering tube (136). The amount of fluid being drawn can be very accurately determined based upon sensors (138). By running each channel pump (32) in isolation, the flow therethrough can be accurately determined based upon the time and the volume of fluid emptied from metering tube (136).

In addition to the input and output devices described above, all of the electrical and electromechanical devices shown are operatively connected to and controlled by control system (20). Specifically, and without limitation, switches and sensors (42, 59, 76, 84, 90, 98, 114, 116, 132 136) provide input (I) to microcontroller (28), which controls the cleaning and/or disinfection cycles and other machine operations in accordance therewith. For example, microcontroller (28) includes outputs (O) that are operatively connected to pumps (32, 38, 70, 72, 88, 94, 100, 110), valves (S1, S2, S3, S5, S6, S7), and heater (80) to control these devices for effective cleaning and/or disinfection cycles and other operations.

Figure 3:
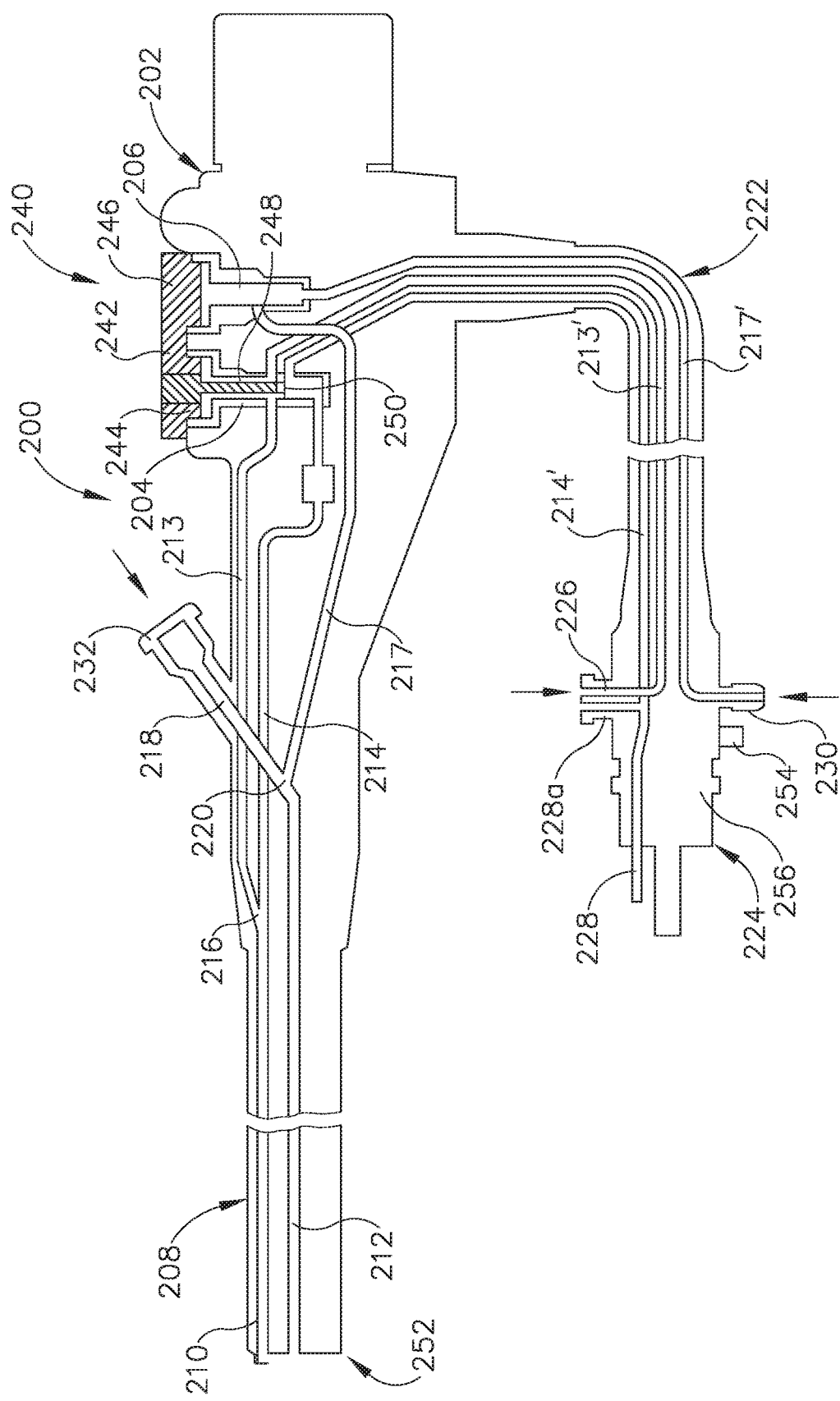
FIG. 3 depicts a cross-sectional side view of proximal and distal portions of an endoscope that may be decontaminated using the reprocessing system of FIG. 1.

As shown in FIG. 3, endoscope (200) has a head part (202). Head part (202) includes openings (204, 206) formed therein. During normal use of endoscope (200), an air/water valve (not shown) and a suction valve (not shown) are arranged in openings (204, 206). A flexible shaft (208) is attached to head part (202). A combined air/water channel (210) and a combined suction/biopsy channel (212) are accommodated in shaft (208). A separate air channel (213) and water channel (214) are also arranged in head part (202) and merge into air/water channel (210) at the location of a joining point (216). It will be appreciated that the term "joining point" as used herein refers to an intersecting junction rather than being limited to a geometrical point and, the terms may be used interchangeably. Furthermore, a separate suction channel (217) and biopsy channel (218) are accommodated in head part (202) and merge into suction/biopsy channel (212) at the location of a joining point (220).

In head part (202), air channel (213) and water channel (214) open into opening (204) for the air/water valve (not shown). Suction channel (217) opens into opening (206) for the suction valve (not shown). Furthermore, a flexible feed hose (222) connects to head part (202) and accommodates channels (213', 214', 217'), which are connected to air channel (213), water channel (214), and suction channel (217) via respective openings (204, 206). In practice, feed hose (222) may also be referred to as the light-conductor casing. The mutually connecting air channels (213, 213') will collectively be referred to below as air channel (213). The mutually connecting water channels (214, 214') will collectively be referred to below as water channel (214). The mutually connecting suction channels (217, 217') will collectively be referred to below as suction channel (217). A connection (226) for air channel (213), connections (228, 228a) for water channel (214), and a connection (230) for suction channel (217) are arranged on the end section (224) (also referred to as the light conductor connector) of flexible hose (222). When the connection (226) is in use, connection (228a) is closed off. A connection (232) for biopsy channel (218) is arranged on head part (202).

A channel separator (240) is shown inserted into openings (204, 206). Channel separator (240) comprises a body (242) and plug members (244, 246), which occlude respective openings (204, 206). A coaxial insert (248) on plug member (244) extends inwardly of opening (204) and terminates in an annular flange (250), which occludes a portion of opening (204) to separate channel (213) from channel (214). By connecting lines (30) to openings (226, 228, 228a, 230, 232), liquid for cleaning and disinfection can be flowed through endoscope channels (213, 214, 217, 218) and out of a distal tip (252) of endoscope (200) via channels (210, 212). Channel separator (240) ensures that such liquid flows all the way through endoscope (200) without leaking out of openings (204, 206); and isolates channels (213, 214) from each other so that each channel (213, 214) has its own independent flow path. One of skill in the art will appreciate that various endoscopes having differing arrangements of channels and openings may require modifications to channel separator (240) to accommodate such differences while occluding ports in head (202) and keeping channels separated from each other so that each channel can be flushed independently of the other channels. Otherwise, a blockage in one channel might merely redirect flow to a connected unblocked channel.

A leakage port (254) on end section (224) leads into an interior portion (256) of endoscope (200) and is used to check for the physical integrity thereof, namely to ensure that no leakage has formed between any of the channels and the interior (256) or from the exterior to the interior (256).

II. Exemplary Medical Device Reprocessing Method with Single-Use Disinfectant

In an exemplary use of reprocessing system (2), an operator may start by actuating a foot pedal (not shown) to open basin lid (16a). Each lid (16a, 16b) may have its own foot pedal. In some versions, once pressure is removed from the foot pedal, the motion of lid (16a, 16b) stops. With lid (16a) open, the operator inserts shaft (208) of endoscope (200) into helical circulation tube (64). End section (224) and head section (202) of endoscope (200) are situated within basin (14a), with feed hose (222) coiled within basin (14a) with as wide a diameter as possible. Next, flush lines (30) are attached to respective endoscope openings (226, 228, 228a, 230, 232). Air line (112) is also connected to connector (254). In some versions, flush lines (30) are color coded, and guide located on station (10) provides a reference for the color-coded connections.

Depending on the customer-selectable configuration, control system (20) may prompt the operator to enter a user code, patient ID, endoscope code, and/or specialist code. This information may be entered manually (e.g., through touch screen (22)), automatically (e.g., by using an attached barcode wand), or in any other suitable fashion. With the information entered (if required), the operator may then close lid (16a). In some versions, closing lid (16a) requires the operator to press a hardware button and a touch-screen (22) button simultaneously to provide a fail-safe mechanism for preventing the operator's hands from being caught or pinched by the closing basin lid (16a). If either the hardware button or software button is released while lid (16a) is in the process of closing, the motion of lid (16a) stops.

Once lid (16a) is closed, the operator presses a button on touch-screen to begin the washing/disinfection process. At the start of the washing/disinfection process, air pump (38) is activated and pressure within the body of endoscope (200) is monitored. When pressure reaches a predetermined level (e.g., 250 mbar), pump (38) is deactivated, and the pressure is allowed to stabilize for a certain stabilization period (e.g., 6 seconds). If pressure has not reached a certain pressure (e.g., 250 mbar) in a certain time period (e.g., 45 seconds), the program is stopped and the operator is notified of a leak. If pressure drops below a threshold (e.g., less than 100 mbar) during the stabilization period, the program is stopped and the operator is notified of the condition. Once the pressure has stabilized, the pressure drop is monitored over the course of a certain duration (e.g., 60 seconds). If the pressure drop is faster than a predetermined rate (e.g., more than 10 mbar within 60 seconds), the program is stopped and the operator is notified of the condition. If the pressure drop is slower than a predetermined rate (e.g., less than 10 mbar in 60 seconds), reprocessing system (2) continues with the next step. A slight positive pressure is held within the body of endoscope (200) during the rest of the process to prevent fluids from leaking in.

A second leak test checks the adequacy of connection to the various ports (226, 228, 228a, 230, 232) and the proper placement of channel separator (240). A quantity of water is admitted to basin (14a) so as to submerge the distal end of endoscope (200) in helical tube (64). Valve (S1) is closed and valve (S7) opened; and pumps (32) are run in reverse to draw a vacuum and to ultimately draw liquid into endoscope channels (210, 212). Pressure sensors (42) are monitored to make sure that the pressure in any one channel (210, 212) does not drop and/or raise by more than a predetermined amount in a given time frame. If it does, it likely indicates that one of the connections was not made correctly and air is leaking into channel (210, 212). In any event, in the presence of an unacceptable pressure drop, control system (20) will cancel the cycle and indicate a likely faulty connection, preferably with an indication of which channel (210, 212) failed.

In the event that the leak tests are passed, reprocessing system (2) continues with a pre-rinse cycle. The purpose of this step is to flush water through channels (210, 212, 213, 214, 217, 218) to remove waste material prior to washing and disinfecting endoscope (200). To initiate the pre-rinse cycle, basin (14a) is filled with filtered water and the water level is detected by pressure sensor (59) below basin (14a). The water is pumped via pumps (32) through the interior of channels (210, 212, 213, 214, 217, 218), directly to drain (74). This water is not recirculated around the exterior surfaces of endoscope 200 during this stage. As the water is being pumped through channels (210, 212, 213, 214, 217, 218), drain pump (72) is activated to ensure that basin (14a) is also emptied. Drain pump (72) will be turned off when drain switch (76) detects that the drain process is complete. During the draining process, sterile air is blown via air pump (38) through all endoscope channels (210, 212, 213, 214, 217, 218) simultaneously, to minimize potential carryover.

Once the pre-rinse cycle is complete, reprocessing system (2) continues with a wash cycle. To begin the wash cycle, basin (14a) is filled with warm water (e.g., approximately 35° C.). Water temperature is controlled by controlling the mix of heated and unheated water. The water level is detected by pressure sensor (59). Reprocessing system (2) then adds enzymatic detergent to the water circulating in reprocessing system (2) by means of peristaltic metering pump (88). The volume is controlled by controlling the delivery time, pump speed, and inner diameter of the tubing of pump (88). Detergent solution (86) is actively pumped throughout the internal endoscope channels (210, 212, 213, 214, 217, 218) and over the outer surface of endoscope (200) for a predetermined time period (e.g., from one to five minutes, or more particularly about three minutes), by channel pumps (32) and external circulation pump (70). Inline heater (80) keeps the temperature at a predetermined temperature (e.g., approximately about 35° C.).

After detergent solution (86) has been circulating for a certain period of time (e.g., a couple of minutes), the flow rate through channels (210, 212, 213, 214, 217, 218) is measured. If the flow rate through any channel (210, 212, 213, 214, 217, 218) is less than a predetermined rate for that channel (210, 212, 213, 214, 217, 218), the channel (210, 212, 213, 214, 217, 218) is identified as blocked, the program is stopped, and the operator is notified of the condition. Peristaltic pumps (32) are run at their predetermined flow rates and cycle off in the presence of unacceptably high pressure readings at the associated pressure sensor (42). If a channel (210, 212, 213, 214, 217, 218) is blocked, the predetermined flow rate will trigger pressure sensor (42), indicating the inability to adequately pass this flow rate. As pumps (32) are peristaltic in the present example, their operating flow rate combined with the percentage of time they are cycled off due to pressure will provide the actual flow rate. The flow rate can also be estimated based upon the decay of the pressure from the time pump (32) cycles off.

At the end of the wash cycle, drain pump (72) is activated to remove detergent solution (86) from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover.

After the wash cycle is complete, reprocessing system (2) begins a rinse cycle. To initiate this rinse cycle, basin (14a) is again filled with warm water (e.g., at approximately 35° C.). Water temperature is controlled by controlling the mix of heated and unheated water. The water level is detected by pressure sensor (59). The rinse water is circulated within channels (210, 212, 213, 214, 217, 218) of endoscope (200) via channel pumps (32); and over the exterior of endoscope (200) via circulation pump (70) and sprinkler arm (60) for a certain period of time (e.g., one minute). As rinse water is pumped through channels (210, 212, 213, 214, 217, 218), the flow rate through channels (210, 212, 213, 214, 217, 218) is measured and if it falls below the predetermined rate for any given channel (210, 212, 213, 214, 217, 218), that channel (210, 212, 213, 214, 217, 218) is identified as blocked, the program is stopped, and the operator is notified of the condition.

At the end of the rinse cycle, drain pump (72) is activated to remove the rinse water from basin (14a) and channels (210, 212, 213, 214, 217, 218), Drain pump (72) turns off when drain level sensor (76) indicates that drainage is complete. During the drain process, sterile air is blown through all channels (210, 212, 213, 214, 217, 218) of endoscope (200) simultaneously to minimize potential carryover. In some versions, the above-described rinsing and draining cycles are repeated at least once again, to ensure maximum rinsing of detergent solution (86) from the surfaces of endoscope (200) and basin (14a).

After reprocessing system (2) has completed the desired number of rinsing and drying cycles, reprocessing system (2) proceeds to a disinfection cycle. To initiate the disinfection cycle, basin (14a) is filled with very warm water at approximately 53° C.). Water temperature is controlled by controlling the mix of heated and unheated water. The water level is detected by pressure sensor (59). During the filling process, channel pumps (32) are off in order to ensure that the disinfectant solution (92) in basin (14a) is at the in-use concentration prior to circulating through channels (210, 212, 213, 214, 217, 218) of endoscope (200).

Next, a measured volume of disinfectant solution (92) is drawn from disinfectant metering pre-chamber (96) and delivered into the water in basin (14a) via metering pump (100). The volume of disinfectant solution (92) is controlled by the positioning of fill level switch (98) relative to the bottom of metering pre-chamber (96). Metering pre-chamber (96) is filled until fill level switch (98) detects liquid. Disinfectant solution (92) is drawn from metering pre-chamber (96) until the level of disinfectant solution (92) in metering pre-chamber (96) is just below the tip of metering pre-chamber (96). After the necessary volume is dispensed, metering pre-chamber (96) is refilled from the bottle of disinfectant solution (92). Disinfectant solution (92) is not added until basin (14a) is filled, so that in case of a water supply problem, concentrated disinfectant is not left on endoscope (200) with no water to rinse it. While disinfectant solution (92) is being added, channel pumps (32) are off in order to ensure that disinfectant solution (92) in basin (14a) is at the desired in-use concentration prior to circulating through channels (210, 212, 213, 214, 217, 218) of endoscope (200).

The in-use disinfectant solution (92) is actively pumped throughout internal channels (210, 212, 213, 214, 217, 218) by pumps (32) and over the outer surface of endoscope (200) by circulation pump (70). This may be done for any suitable duration (e.g., at least 5 minutes), The temperature of the disinfectant solution (92) may be controlled by in-line heater (80) to stay at a consistent temperature (e.g., about 52.5° C.). During the disinfection process, flow through each channel (210, 212, 213, 214, 217, 218) of endoscope (200) is verified by timing the delivery of a measured quantity of solution through channel (210, 212, 213, 214, 217, 218). Valve (S1) is closed, and valve (S7) opened, and in turn each channel pump (32) delivers a predetermined volume to its associated channel (210, 212, 213, 214, 217, 218) from metering tube (136). This volume and the time it takes to deliver the volume, provides a very accurate flow rate through the channel (210, 212, 213, 214, 217, 218). Anomalies in the flow rate from what is expected for a channel (210, 212, 213, 214, 217, 218) of that diameter and length are flagged by control system (20) and the process stopped. As in-use disinfectant solution (92) is pumped through channels (210, 212, 213, 214, 217, 218), the flow rate through channels (210, 212, 213, 214, 217, 218) is also measured as described above.

At the end of the disinfection cycle, drain pump (72) is activated to remove disinfectant solution (92) solution from basin (14a) and channels (210, 212, 213, 214, 217, 218). During the draining process, sterile air is blown through all channels (210, 212, 213, 214, 217, 218) of endoscope (200) simultaneously to minimize potential carryover.

After disinfectant solution (92) has been drained from basin (14a), reprocessing system (2) begins a final rinse cycle. To initiate this cycle, basin (14a) is filled with sterile warm water (e.g., at approximately 45° C.) that has been passed through a filter (e.g., a 0.2 μm filter). The rinse water is circulated within channels (210, 212, 213, 214, 217, 218) by pumps (32); and over the exterior of endoscope (200) via circulation pump (70) and sprinkler arm 60) for a suitable duration (e.g., 1 minute). As rinse water is pumped through channels (210, 212, 213, 214, 217, 218), the flow rate through channels (210, 212, 213, 214, 217, 218) is measured as described above. Drain pump (72) is activated to remove the rinse water from basin (14a) and channels (210, 212, 213, 214, 217, 218). During the draining process, sterile air is blown through all channels (210, 212, 213, 214, 217, 218) of endoscope (200) simultaneously to minimize potential carryover. In some versions, the above-described rinsing and draining cycles are repeated at least two more times, to ensure maximum rinsing of disinfectant solution (92) residuals from the surfaces of endoscope (200) and basin (14a).

After the final rinse cycle is complete, reprocessing system (2) begins a final leak test. In particular, reprocessing system (2) pressurizes the body of endoscope (200) and measures the leak rate as described above. If the final leak test is successful, reprocessing system (2) indicates the successful completion of the cycles via touch-screen (22). From the time of program completion to the time at which lid (16a) is opened, pressure within the body of endoscope (200) is normalized to atmospheric pressure by opening vent valve (S5) at a predetermined rate (e.g., valve (S5) opened for 10 seconds every minute).

Depending on customer-selected configuration, reprocessing system (2) may prevent lid (16a) from being opened until a valid user identification code is entered. Information about the completed program, including the user ID, endoscope ID, specialist ID, and patient ID are stored along with the sensor data obtained throughout the program. If a printer is connected to reprocessing system (2), and if requested by the operator, a record of the disinfection program will be printed. Once a valid user identification code has been entered, lid (16a) may be opened (e.g., using the foot pedal as described above). Endoscope (200) is then disconnected from flush lines (30) and removed from basin (14a). Lid (16a) can then be closed using both the hardware and software buttons as described above.

III. Exemplary Medical Device Reprocessing with Reusable Disinfectant

In some instances, it may be desirable to collect and reuse disinfectant one or more times rather than drain and dispose of the disinfectant after a single use. For example, reusing disinfectant uses less total disinfectant over the useful life of reprocessing system (2) and may thus decrease the overall cost of operation. In addition, concentrated disinfectant, such as the disinfectant provided from disinfectant storage (92), may have a damaging effect on one or more portions of reprocessing system (2) until mixed with water as a disinfectant solution in the desired concentrations. Storing and reusing the disinfectant solution thus reduces the presence of concentrated disinfectant and may thus increase the useful life of reprocessing system (2).

Figure 4:
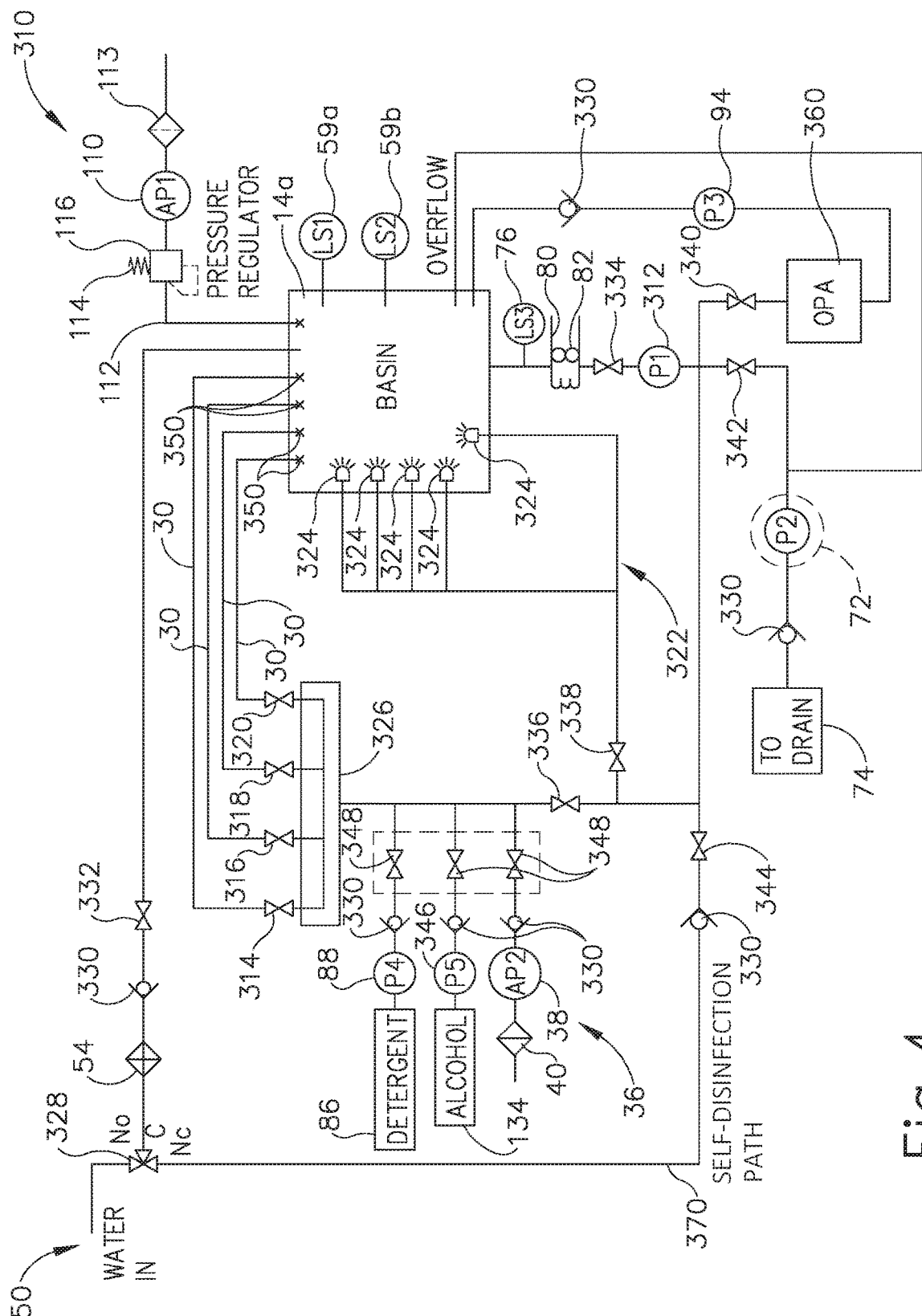
FIG. 4 depicts a schematic diagram of a second exemplary reprocessing system.

FIG. 4 shows an exemplary reprocessing system (310) that has a disinfectant storage reservoir (360) from which to pump the disinfectant to basin (14a) and collect the disinfectant after completion of the disinfection cycle. Alternative versions of reprocessing system (410, 510, 610) discussed herein also include exemplary disinfection storage reservoir (360). It will be appreciated that various aspects of reusing disinfectant may be used with respect to any of reprocessing systems (2, 310, 410, 510, 610) and in any combination as described herein.

As shown in FIG. 4, reprocessing system (310) includes primary pump (312) that receives the fluid, such as the water and/or disinfectant, and pumps the fluid toward the collection of valves (336, 338, 340, 342, 344) as discussed above with respect to various cycles. More particularly, disinfection valve (340) is configured to transition between a circulation state and a collection state during the disinfection cycle. With disinfection valve (340) in the circulation state, the collection of valves (336, 338, 340, 342, 344) is configured to return disinfectant toward flush lines (30) and nozzle assembly (322) for continued circulation during reprocessing. At the conclusion of the disinfection cycle, disinfection valve (340) transitions from the circulation state to the collection state and, in conjunction with the remaining collection of valves (336, 338, 342, 344), directs the disinfectant into disinfectant storage reservoir (360) for reuse in future disinfection cycles. As used herein, the term "disinfectant" refers to concentrated disinfectant or any solution including disinfectant at any concentration. The term "disinfectant" is thus not intended to unnecessarily limit the invention to a particular concentration or solution of disinfectant. Also, while the examples discussed herein are provided in the context of disinfectant, the same teachings may be readily applied to detergent that is circulated through at least a portion of reprocessing system (310).

Reprocessing system (310) further includes disinfectant pump (94) in fluid communication between disinfectant storage reservoir (360) and basin (14a). Disinfectant pump (94) thus pumps the disinfectant directly into basin (14a). Check valve (330) is also fluidly connected between basin (14a) and disinfectant pump (94) and is configured to inhibit fluid within basin (14a) from flowing backward toward pump (94). In some versions, disinfectant storage reservoir (360) is in the form of a break tank such that primary pump (312) and disinfectant pump (94) are configured to individually and/or simultaneously interact with disinfectant storage reservoir (360). However, it will be appreciated that alternative couplings and other features may be used to fluidly couple any form of disinfectant storage reservoir (360) within reprocessing system (310) for collecting and reusing disinfectant. The invention is thus not intended to be limited to the particular disinfectant storage reservoir (360).

Reprocessing system (310) of this example may be readily incorporated into stations (10, 12) (see FIG. 1) with basins (14a, 14b). Basin (14a) shown in FIG. 4 thus receives water from water source (50) and discharges all water therefrom via drain (74), as discussed above. Exemplary basin (14a) includes a plurality of flush lines (30) extending therein and a nozzle assembly (322) having a plurality of nozzles (324). Each flush line (30) and nozzle (324) is configured to direct the water and/or any additive solution, which may be generally referred to as the fluid, toward endoscope (200) (see FIG. 3) within basin (14a) for reprocessing. As discussed above, flush lines (30) are configured to discharge the fluid into respective channels (210, 212, 217, 218) (see FIG. 3), at respective predetermined conduit flow rates particularly configured for each respective channel (210, 212, 217, 218) (see FIG. 3). To this end, primary pump (312) pumps a predetermined supply flow rate of the fluid collectively to flush lines (30) via a common manifold (326) that is fluidly coupled therebetween.

A plurality of flush valves (314, 316, 318, 320) are positioned respectively in each flush line (30) and are collectively configured to balance fluid flow from primary pump (312) such that each flush line (30) discharges fluid therefrom at respective predetermined conduit flow rates. In some versions, flush lines (30) deliver four different respective predetermined conduit flow rates of fluid to channels (210, 212, 217, 218) (see FIG. 3). In some other versions, one or more of the respective predetermined conduit flow rates are approximately equivalent to accommodate an alternative medical device. In any case, any number of flush lines (30) configured to deliver fluid at any predetermined conduit flow rates may be used to accommodate one or more types of medical devices.

Water source (50) delivers the water to a three-way introduction valve (328), which directs the water through filter (54), check valve (330), and two-way valve (332) into basin (14a). As in reprocessing system (2) (see FIG. 2), the water may be collected to a desirable amount as detected by level sensors (59a, 59b, 76). The water drains from basin (14a) and may pass through heater (80) and two-way valve (334) to reach primary pump (312) for distribution toward flush lines (30) and nozzle assembly (322). More particularly, a collection of two-way valves (336, 338, 340, 342, 344) are fluidly connected downstream of primary pump (312) to either allow or inhibit fluid flow therethrough for various cycles as discussed herein. For example, flush valve (336) and nozzle valve (338) are configured to control flow respectively toward flush lines (30) and nozzle assembly (322).

In addition, disinfectant valve (340), drain valve (342), and return valve (344) are respectively configured to provide disinfection of endoscope (200), drainage from reprocessing system (310), and self-disinfection of reprocessing system (310). Disinfection and self-disinfection will be discussed below in additional detail. In the present example, disinfection valve (340), drain valve (342), and return valve (344) are presumed fully closed so as to direct the entirety of the predetermined supply flow of the fluid through the opened flush and nozzle valves (336, 338). However, the collection of valves (336, 338, 340, 342, 344) may be fully opened, partially opened, and/or fully closed so as to direct the fluid in any one of a plurality of desirable ratios to complete the cycles of reprocessing. The invention is thus not intended to be limited specifically to the combination of open and/or closed valves as described herein.

Downstream of flush valve (336), additive storages, such as detergent and alcohol storage (86, 134), and detergent metering pump (88), an alcohol metering pump (346), and a gas pump (38) fluidly connect to be received with or in place of water flowing toward flush lines (30). A series of optional two-way valves (348) may be fluidly connected downstream of pumps (88, 346, 38) for additional flow control of various additives. In any case, the fluid, such as water, is received within manifold (326) at the predetermined supply flow rate. As shown in exemplary reprocessing system (310) of FIG. 4, each of the four flush lines (30) fluidly connects to manifold (326) and extends into basin (14a) for connection with channels (210, 212, 217, 218) (see FIG. 3) of endoscope (200). More particularly, each flush line (30) includes a coupling port (350) within basin (14a) that is configured to fluidly seal against endoscope (200) for fluidly coupling channels (210, 212, 217, 218) (see FIG. 3) with respective flush lines (30).

As briefly discussed above, each flush line (30) includes its respective flush valve (314, 316, 318, 320) configured to balance fluid flows along flush lines (30) according to the predetermined conduit flow rates. In some versions, flush valves (314, 316, 318, 320) are in the form of orifice valves that are sized relative to each to each other to create predetermined restriction on the fluid entering manifold (326) according to the predetermined supply flow rate. As the pressure within the manifold (326) distributes equally through flush lines (30), predetermined conduit flow rates of fluid flow through each respective flush valve (314, 316, 318, 320) and discharge from coupling ports (350). Alternatively, flush valves (314, 316, 318, 320) may each comprise a variable valve configured to provide a discrete, predetermined flow rate so that the operator may adjust various flow rates to accommodate differing medical devices in reprocessing system (310).

Furthermore, nozzle valve (338) also receives the fluid, such as water, from primary pump (312) and directs the fluid toward nozzle assembly (322). Each nozzle (324) is generally identical in the present example and configured to discharge fluid onto the exterior of endoscope (200) (see FIG. 3) within basin (14a) at approximately equivalent predetermined nozzle flow rates. To this end, nozzle valve (338) is configured to further balance the predetermined supply flow rate of fluid with flush valves (314, 316, 318, 320) such that each nozzle (324) and fluid line (30) discharges fluid therefrom according to its predetermined conduit flow rate and predetermined nozzle flow rate, respectively. Similar to flush valves (314, 316, 318, 320), nozzle valve (338) may also be a variable valve configured to set to a discrete, predetermined flow rate so that the operator may adjust various flow rates to accommodate differing medical devices in reprocessing system (310). Alternatively, nozzle valve (338) in an open position may provide negligible resistance such that the various predetermined flow rates are balanced simply by restriction in each respective nozzle (324).

In use, reprocessing system (310) receives water from water supply (50) into basin (14a). Alternatively, basin (14a) may receive one of the additives alone or in combination with the water. In any case, the fluid collected within basin (14a) is received within primary pump (312) and pumped therefrom at the predetermined supply flow rate. The collection of valves (338, 340, 342, 344) are generally configured to direct the fluid at the predetermined supply flow rate toward manifold (326) and nozzle assembly (322). The fluid flowing toward manifold (326) may also receive one of the additives, such as detergent, as discussed above in additional detail.

A predetermined portion of the fluid flows into manifold (326), while a remaining predetermined portion of the fluid flows through nozzle valve (338). Flush valves (336) and nozzle valve (338) generate predetermined restriction in each respective flush line (30) in order to direct fluid flow along each flush line (30) with at least two different respective predetermined conduit flow rates. Such predetermined restriction and restriction results in flush valves (336) and nozzle valve (338) apportioning the fluid flow therethrough according to the various predetermined flow rates. For example, flush valves (336) and nozzle valve (338) may be configured to direct fluid along four flush lines (30) with four different respective predetermined conduit flow rates. Once balanced accordingly, the fluid discharges from each coupling port (350) and into respective channels (210, 212, 217, 218) (see FIG. 3) with the predetermined conduit flow rates for reprocessing endoscope (200) (see FIG. 3). It will be appreciated that generating such predetermined flow rates via valves (336, 338) may be used in any cycle of reprocessing described herein and is not intended to limit the invention to any specific reprocessing cycle.

Reprocessing system (310) of the present example includes only one primary pump (312) supplying the predetermined supply flow rate of fluid to each flush line (30) and nozzle (324). However, it will be appreciated that any number of pumps may be used in combination, such as in series or parallel, to direct fluid as discussed above. It will therefore be appreciated that the invention is not intended to unnecessarily be limited to only one primary pump (312). By way of further example only, reprocessing system (310) may be configured and operable in accordance with at least some of the teachings of U.S. patent application Ser. No. 15/157,800, entitled "Apparatus and Method for Reprocessing a Medical Device," filed on May 18, 2016, the disclosure of which is incorporated by reference herein.

Figure 5:
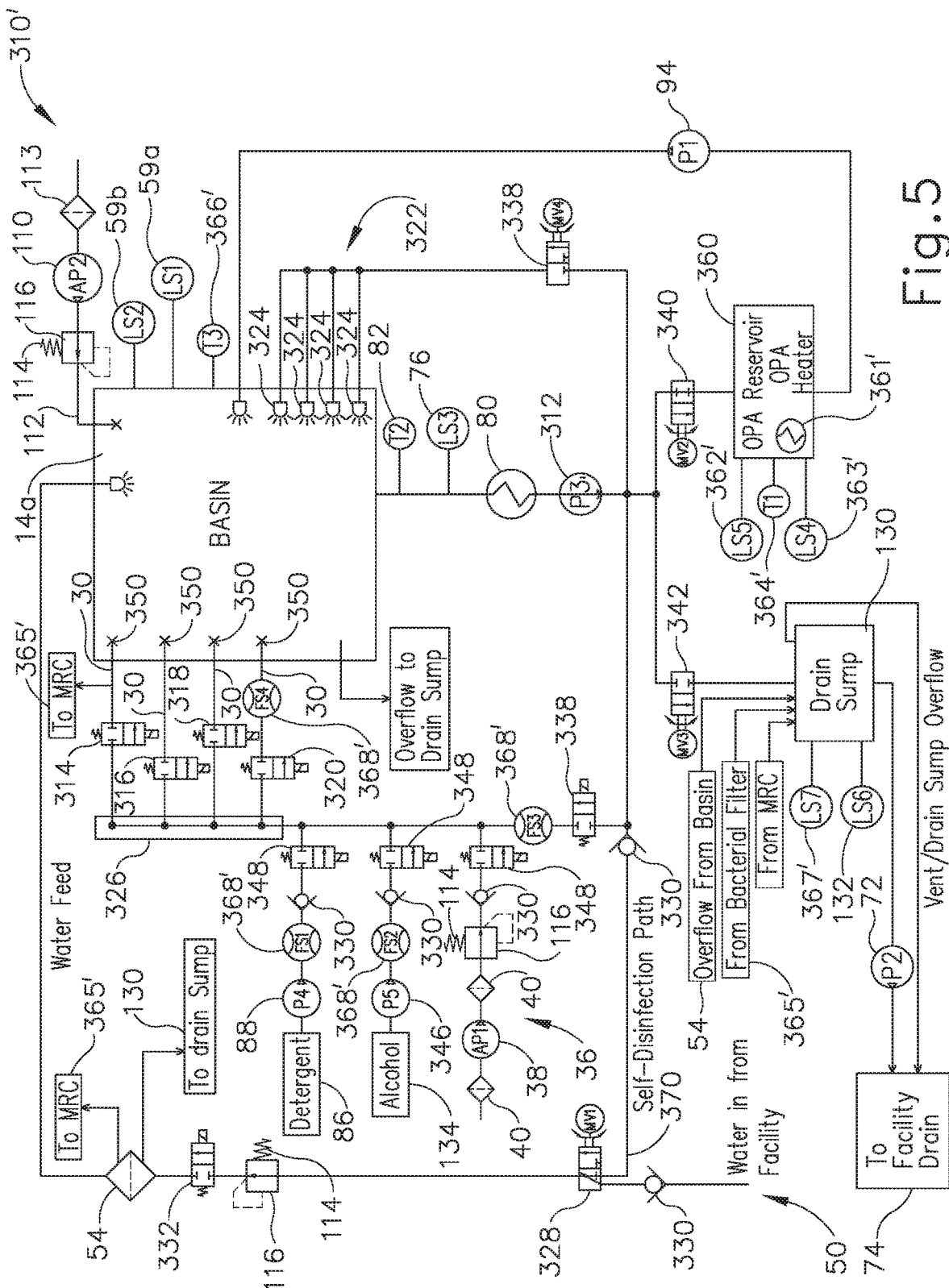
FIG. 5 depicts a schematic diagram of a third exemplary reprocessing system.

FIG. 5 shows another exemplary reprocessing system (310'), which has another exemplary disinfectant storage reservoir (360') fluidly connected between disinfectant valve (340) and pump (94). Disinfectant storage reservoir (360') is generally similar to disinfectant storage reservoir (360) (see FIG. 4), but also includes additional features for further preparing and maintaining the disinfectant for reprocessing. Specifically, disinfectant storage reservoir (360') includes a disinfectant heater (361') that is configured to heat the disinfectant for reprocessing. In some versions, disinfectant heater (361') is configured to pre-heat the disinfectant in anticipation of use in order to more quickly heat the fluid circulating through reprocessing system (310') for reasons discussed below in additional detail. Alternatively or in addition, disinfectant heater (361') may heat the disinfectant while flowing from disinfectant storage reservoir (360') toward pump (94) for use. In either case, disinfectant heater (361') may be configured to heat the fluid in conjunction with heater (80) for collectively heating the fluid as it flows through reprocessing system (310').

Disinfectant storage reservoir (360') further includes a maximum level sensor (362'), a minimum level sensor (363'), and a temperature sensor (364') for monitoring the disinfectant flowing through and/or contained within disinfectant storage reservoir (360'). Maximum and minimum level sensors (362', 363') are configured to approximate the amount of disinfectant contained within disinfectant storage reservoir (360') and communicate with another system, such as control system (20) (see FIG. 1). For example, maximum and minimum level sensors (362', 363') and control system (20) (see FIG. 1) collectively monitor the amount of disinfectant to be above the maximum level, below the minimum level, or between the maximum and minimum levels, which is generally desired for operation. Temperature sensor (364') also communicates with another system, such as control system (20) (see FIG. 1), to monitor the temperature of the disinfectant.

In order to further monitor the disinfectant, reprocessing system (310') also includes a disinfectant concentration measuring subsystem (365') that is configured to receive the disinfectant from at least one location within reprocessing system (310') for sampling and testing. To this end, disinfectant concentration measuring subsystem (365') of the present example receives the disinfectant samples from filter (54) and from at least one of flush lines (30). Disinfectant concentration measuring subsystem (365') is configured to test samples of disinfectant received from filter (54) and flush line (30) for a concentration of disinfectant present within the fluid flowing therethrough. In the event that the measured concentration of disinfectant is not within a predetermined range of concentration or is below a predetermined minimum concentration, disinfectant concentration measuring subsystem (365') notifies the operator accordingly. Such measurement and notification may be further aided by communication with control system (20) (see FIG. 1) discussed above in greater detail.

Upon completion of sampling and testing, the disinfectant drains to drain sump (130) such that disinfectant concentration measuring subsystem (365') is available for further use. In parallel, filter (54) also drains directly to drain sump (130) in the event that fluid is not directed toward disinfectant concentration measuring subsystem (365'). It will be appreciated that various devices and method for measuring disinfectant concentration and notifying the operator may be used as described herein and, as such, the invention is not intended to be unnecessarily limited to any particular disinfectant concentration measuring subsystem. By way of further example only, disinfectant concentration measuring subsystem (365') may be configured and operable in accordance with at least some of the teachings of U.S. patent application Ser. No. 15/157,952, entitled "Apparatus and Method to Measure Concentration of Disinfectant in Medical Device Reprocessing System," filed on May 18, 2016, the disclosure of which is incorporated by reference herein.

Additional monitoring is provided in reprocessing system (310') by a basin temperature sensor (366'), a drain sump overflow sensor (367'), and a plurality of flow sensors (368'). Basin temperature sensor (366') is generally configured to measure the temperature of fluid therein, while drain sump overflow sensor (367') is configured to measure an excess of fluid collected within drain sump (130) for alerting the operator. Each flow sensor (368') is configured to measure the volumetric flow rate of fluid flowing therethrough for monitoring the overall circulation of fluid through reprocessing system (310'). Each of temperature sensor (366'), drain sump overflow sensor (367'), and flow sensors (368') may communicate with control system (20) (see FIG. 1) for collective operation with any one or more of the sensors discussed herein for using reprocessing system (310). However, it will be appreciated that alternative devices and methods of monitoring reprocessing system (310') may be used and that the invention described herein is not intended to be unnecessarily limited to reprocessing system (310').

IV. Exemplary Medical Device Reprocessing Apparatus and Method for Separate Internal and External Disinfection As discussed above, concentrated disinfectant, such as the disinfectant provided from disinfectant storage (92, 360), may have a damaging effect on certain structures until the concentrated disinfectant is mixed with water as a disinfectant solution in the desired concentrations. Endoscopes such as endoscope (200) referenced above, include among other components an outer surface and one or more internal channels (210, 212, 213, 214, 217, 218). The outer surfaces of some endoscopes (200) may be formed of a material or coating that is particularly sensitive and/or susceptible to high concentration chemicals, such as high concentration disinfectant (92), or high temperatures. As merely an illustrative example, the outer surfaces of endoscopes (200) may be formed of polyurethane or aluminum. Additionally, due to the ease in accessing the outer surface of endoscopes (200), a high concentration disinfectant is not required to effectively decontaminate this portion of endoscope (200). Thus, utilizing a low concentration of disinfectant or detergent may be desirable to effectively achieve bioburden reduction along the outer surfaces of endoscopes (200) while preserving the lifespan of endoscope (200).

By contrast, internal channels (210, 212, 213, 214, 217, 218) of endoscopes (200) are formed of a material that is more tolerant of chemicals such as high concentration disinfectant (92) than the outer surfaces of endoscopes (200). As merely an illustrative example, internal channels (210, 212, 213, 214, 217, 218) may be formed of Teflon or metals that have a higher tolerance to chemical or heat exposure. Accordingly, internal channels (210, 212, 213, 214, 217, 218) are capable of being exposed to a higher concentration of disinfectant or detergent and/or a higher temperature. Additionally, due to the narrow configuration, and sometimes irregular profile, of internal channels (210, 212, 213, 214, 217, 218) of endoscopes (200), utilizing a higher level of concentration may be desirable to effectively achieve bioburden reduction within internal channels (210, 212, 213, 214, 217, 218) due to the greater difficulty in disinfecting internal channels (210, 212, 213, 214, 217, 218) than the outer surface of endoscope (200).

To ensure a sufficient margin of safety in decontaminating endoscopes (200), it may be desirable to apply varying concentrations of disinfectant and varying levels of temperature to the outer surface and internal channels (210, 212, 213, 214, 217, 218) of endoscopes (200) and other similar instruments. Providing the same concentration of disinfectant or heat for both the internal and external components of endoscope (200) may not effectively decontaminate the instrument thereby increasing the possibility of infection or illness due to a patient's exposure to a contaminated instrument. The following description provides various examples of a reprocessing system configured to deliver different concentrations of disinfectant to particular components of a medical instrument within the same overall cycle. As noted above, while the below teachings are provided in the context of delivering disinfectant to the outer surface and internal channels (210, 212, 213, 214, 217, 218) of endoscopes (200) and other similar instruments, the same teachings may be readily applied to delivery of detergent to the outer surface and internal channels (210, 212, 213, 214, 217, 218) of endoscopes (200) and other similar instruments.

A. Time Based Medical Device Reprocessing Apparatus and Method

In some instances, it may be desirable to ensure a sufficient degree of decontamination has been achieved in the internal channels and outer surface of an endoscope by exposing the endoscope to a biocide or disinfectant for a predetermined time threshold. A reprocessing method that entails depositing a disinfectant within the internal channels of an endoscope for a set duration may be beneficial to adequately disinfect the inner components of the endoscope to thereby achieve a sufficient level of biocidal activity. Subjecting the outer surfaces of an endoscope for a predetermined period of decontamination may be beneficial to achieve a higher level of bioburden reduction without damaging the external surface of the endoscope.

The following description provides various examples of a reprocessing method configured to adequately decontaminate the internal channels and outer surface of multiple endoscopes based on a predetermined duration of exposure. Ultimately, providing a methodical approach to disinfecting the inner components and external area of an endoscope may be beneficial to ensure that the proper degree of bioburden reduction is achieved in each cycle. It should be understood that the reprocessing method described below may be readily incorporated into any of the various reprocessing systems (2, 310, 310') and to any of the various endoscopes (200) described above. Other suitable ways in which the below described reprocessing method may be used will be apparent to those of ordinary skill in the art in view of the teachings herein.

Figure 6:
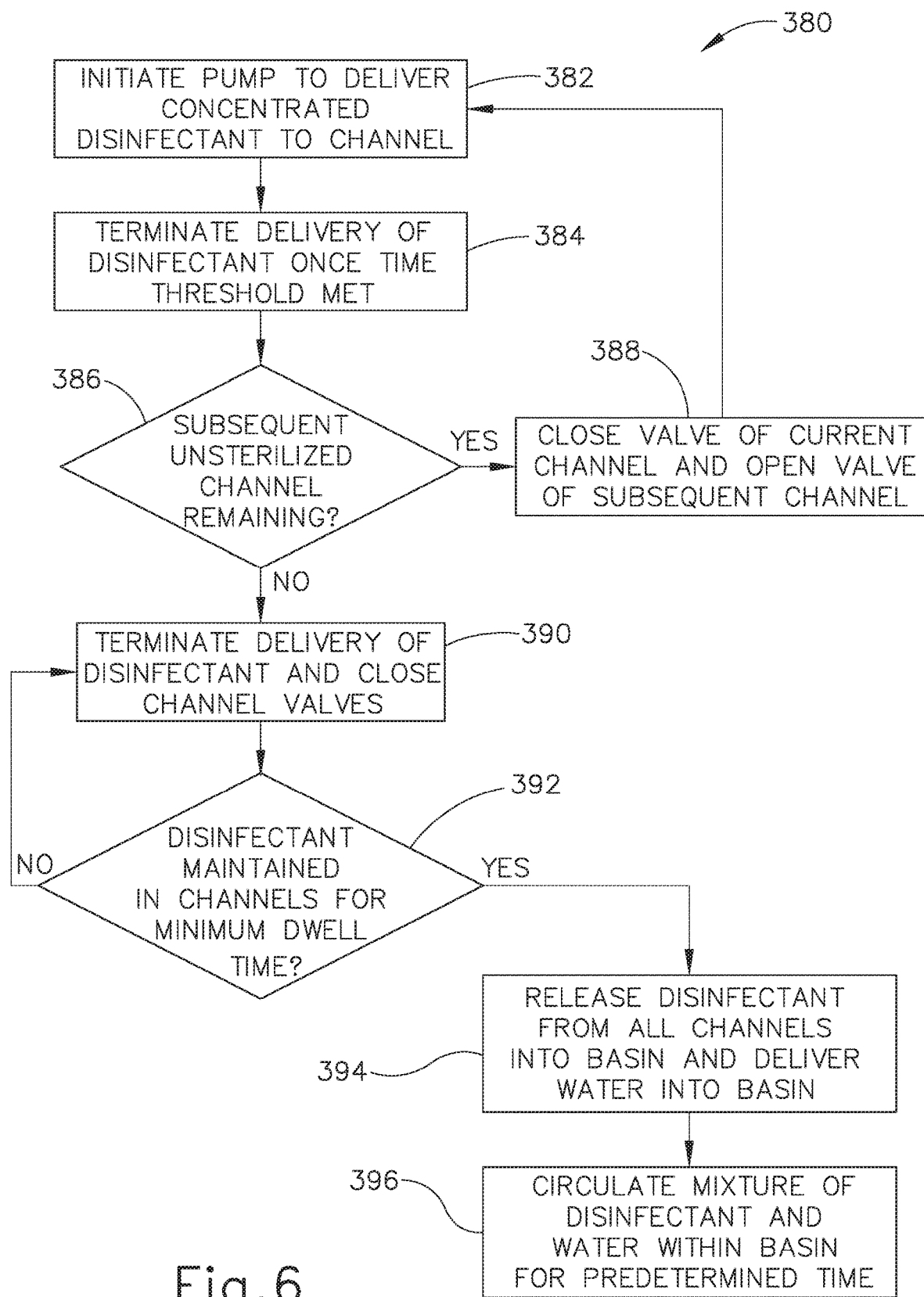
FIG. 6 depicts a flow diagram illustrating an exemplary reprocessing method utilized by the reprocessing system of FIG. 1, with the internal channels of the endoscopes decontaminated with a disinfectant solution prior to being reused to decontaminate the exterior surfaces of the endoscopes.

FIG. 6 shows a flow diagram illustrating steps of an exemplary reprocessing method (380) that may be used by reprocessing system (2, 310, 310') to perform a disinfection cycle of the internal channels (210, 212, 213, 214, 217, 218) and external surface of one or more endoscopes (200). After reprocessing system (2, 310, 310') has completed the desired number of rinsing and drying cycles, pump (32, 312) delivers concentrated disinfectant (92) to internal channels (210, 212, 213, 214, 217, 218) of a first endoscope (200), as seen at step (382). At step (384), the concentrated disinfectant (92) continues to be delivered by pump (32, 312) to internal channels (210, 213, 214, 217, 218) until a predetermined time threshold has been reached. Once the predetermined time threshold has elapsed, pump (32, 312) ceases delivering disinfectant (92) to internal channels (210, 212, 213, 214, 217, 218) and reprocessing system (2, 310, 310') determines whether any other contaminated internal channels (210, 212, 213, 214, 217, 218) remain, as seen at step (386).

At step (388), reprocessing system (2, 310, 310') closes flush valve (314) of the first endoscope (200) and subsequently opens flush valve (316) of the other internal channels (210, 212, 213, 214, 217, 218) which remain contaminated. Reprocessing system (2, 310, 310') will continue to perform step (382) through step (388) until reprocessing system (2, 310, 310') determines that no additional, contaminated internal channels (210, 212, 213, 214, 217, 218) remain to be cleaned at step (386). In this instance, at step (390), the last flush valve (320) connecting to the last, disinfected internal channel (210, 212, 213, 214, 217, 218) is closed. At step (392), the concentrated disinfectant (92) remains in the respective internal channels (210, 212, 213, 214, 217, 218) until a predetermined dwell time elapses. As merely an illustrative example, the predetermined dwell time can range between approximately 10 seconds to 30 minutes. Once reprocessing system (2, 310, 310') determines that the predetermined dwell time has elapsed, at step (394), the concentrated disinfectant (92) contained in the respective internal channels (210, 212, 213, 214, 217, 218) of is released into basin (14a).

Simultaneously, at step (396), water is delivered from water source (50) into basin (14a) as the concentrated disinfectant (92) is released from internal channels (210, 212, 213, 214, 217, 218) into basin (14a). For example, concentrated disinfectant (92) may be released or pushed out from internal channels (210, 212, 213, 214, 217, 218) by flushing air or water through internal channels (210, 212, 213, 214, 217, 218). Other various suitable ways to release concentrated disinfectant (92) from internal channels (210, 212, 213, 214, 217, 218) will be apparent to those of ordinary skill in the art in view of the teachings herein.

At step (396), the concentrated disinfectant (92) and water in basin (14a) are circulated by circulation pump (70) thereby mixing the substances together and effectively diluting disinfectant (92) from an initial concentration to a lower concentrated disinfectant solution (92). In this instance, with endoscope (200) being positioned within basin (14a), the outer surface of endoscope (200) is exposed to diluted disinfectant solution (92) being circulated throughout basin (14a) thereby providing disinfection of the outer surface of endoscope (200) after internal channels (210, 212, 213, 214, 217, 218) have been fully decontaminated. Circulation pump (70) will continue to pump diluted disinfectant solution (92) over the outer surface of endoscope (200) until a predetermined duration has elapsed.

At the end of the disinfection cycle, drain pump (72) is activated to remove diluted disinfectant solution (92) solution from basin (14a). During the draining process, sterile air is blown through all channels (210, 212, 213, 214, 217, 218) of endoscope (200) simultaneously to minimize potential carryover. After diluted disinfectant solution (92) has been drained from basin (14a), reprocessing system (2, 310, 310') begins a final rinse cycle as discussed in detail above.

B. Measurement Based Reprocessing Apparatus and Method

In some instances, it may be desirable to achieve a sufficient degree of decontamination in the internal channels of an endoscope by delivering a measured amount of biocide or disinfectant that directly corresponds to the respective volume of the internal channel. In this instance, associating the quantity of disinfectant delivered to the internal channels of an endoscope with the volume of the internal channels may be beneficial to minimize occurrences of under-delivery to any given channel. Determining the amount of concentrated disinfectant delivered to the internal channels in accordance with the respective volume of each channel may be beneficial to ensure that the entirety of the lumen of each channel is exposed to disinfectant, rather than the amount being in accordance with an arbitrary element that does not take the characteristics of the particular channel into consideration.

The following description provides various examples of a reprocessing method that is configured to adequately decontaminate the internal channels of multiple endoscopes based on the capacity of the internal channels. Ultimately, providing a variable approach to disinfecting internal channels with varying dimensions may be beneficial to ensure that the proper degree of bioburden reduction is achieved in each instance. It should be understood that the reprocessing method described below may be readily incorporated into any of the various reprocessing systems (2, 310, 310') and to any of the various endoscopes (200) described above. Other suitable ways in which the below-described reprocessing method may be used will be apparent to those of ordinary skill in the art in view of the teachings herein.

Figure 7:
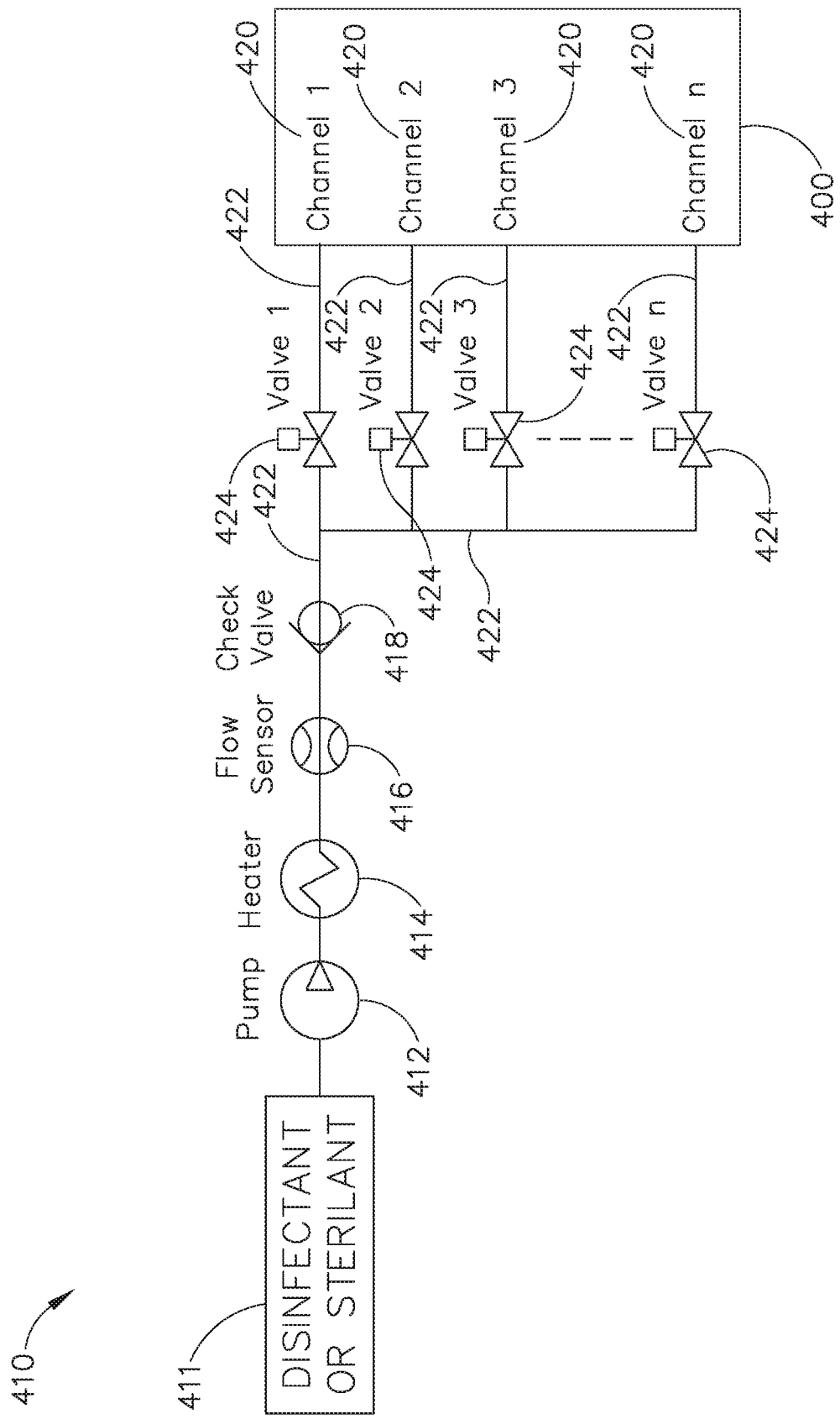
FIG. 7 depicts a partial schematic diagram of an exemplary variation of the reprocessing system of FIG. 1 including a single flow sensor monitoring multiple endoscope channels.

FIG. 7 shows a block schematic of an exemplary reprocessing system (410) including a disinfectant storage (411), a disinfectant pump (412), an inline heater (414), a flow sensor (416), and a check valve (418). Except as otherwise described below, reprocessing system (410), disinfectant storage (411), disinfectant pump (412), inline heater (414), and check valve (418) are configured and operable just like reprocessing system (2, 310, 310'), disinfectant storage (92, 360), disinfectant pump (94), inline heater (80), and check valve (330), respectively, described above. Several internal channels (420) of an endoscope (400) are in fluid communication with disinfectant storage (411) via flush lines (422). Flush lines (422) include one or more flush valves (424) in line downstream of check valve (418) for each channel (120) operatively connected to reprocessing system (410).

Reprocessing system (410) is operable to individually deliver a concentrated level of disinfectant (92) to internal channels (420) of endoscope (400). In particular, flow sensor (416) is operable to monitor and measure the quantity of concentrated disinfectant (92) delivered from disinfectant pump (412) to internal channels (420). Control system (20) is configured to receive and analyze data transmitted by flow sensor (416) to determine when to close a particular flush valve (424) that is in fluid connection with the first channel (420). In other words, control system (20) is operable to identify the volume of the first channel (420) of endoscope (400) and close flush valve (424) that is in communication with first channel (420) once a corresponding amount of concentrated disinfectant (92) is delivered to that particular channel (420). In this instance, reprocessing system (410) is configured to open a subsequent flush valve (424) that is in fluid connection with a subsequent internal channel (420) that has not yet received concentrated disinfectant (92). Valves (424) may thus be opened and closed in a sequence to sequentially deliver concentrated disinfectant (92) to channels (420). While only one endoscope (400) is shown as being reprocessed in reprocessing system (410), it should be understood that reprocessing system (410) may be capable of reprocessing more than one endoscope (400) simultaneously and/or in a sequence.

Figure 8:
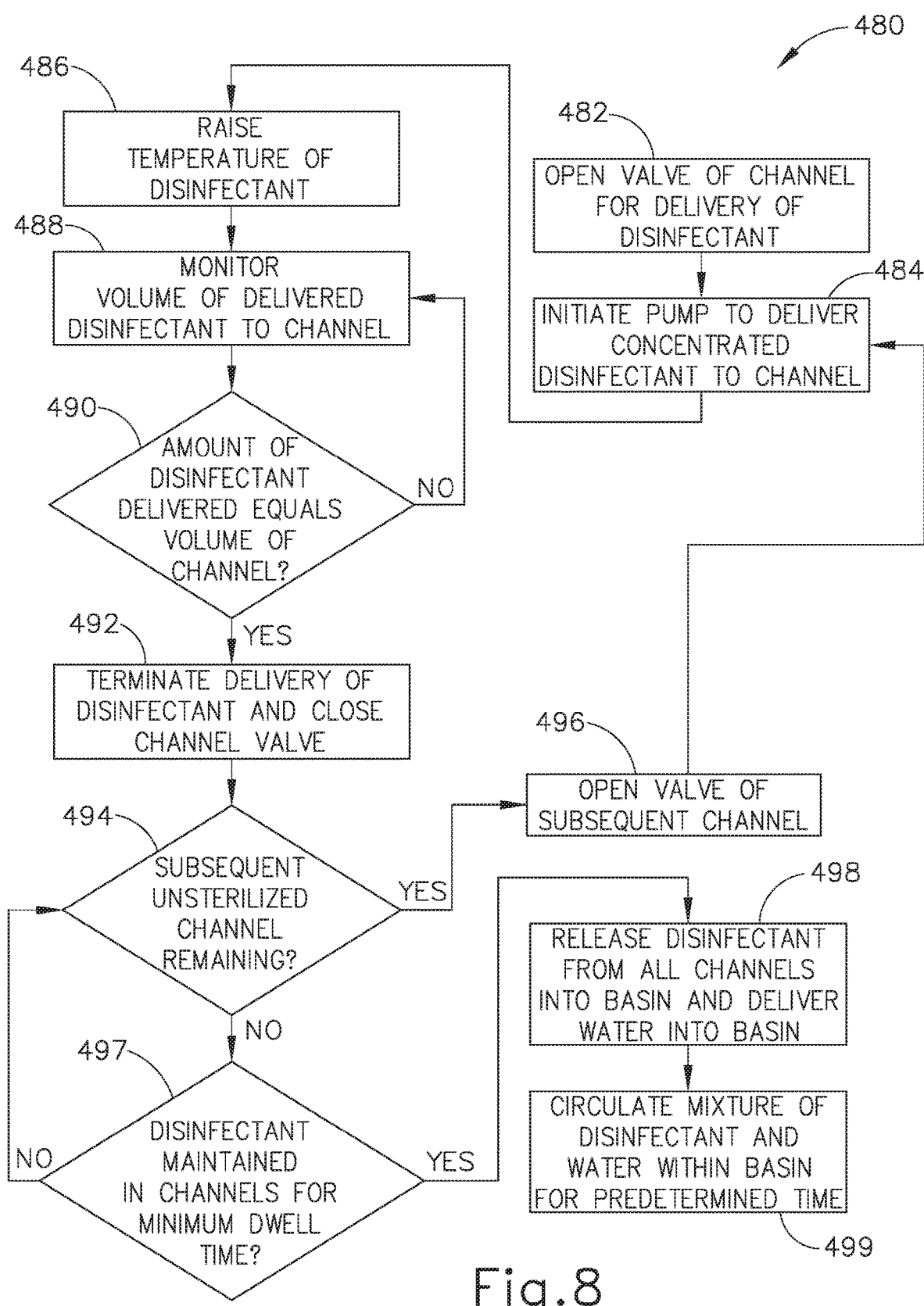
FIG. 8 depicts a flow diagram illustrating another exemplary reprocessing method utilized by the reprocessing system of FIG. 7, with a flow sensor monitoring the volume of disinfectant delivered to the open channel of an endoscope.

FIG. 8 shows a flow diagram illustrating steps of an exemplary reprocessing method (480) that may be used by reprocessing system (410) to perform a disinfection cycle of internal channels (420) and the external surface of one or more endoscopes (400). After reprocessing system (410) has completed the desired number of rinsing and drying cycles, reprocessing system (410) opens a first flush valve (424) in fluid connection with a first channel (420) through flush lines (422), as seen at step (482). At step (484), disinfectant pump (412) delivers concentrated disinfectant (92) to internal channel (420). In this instance, as seen at step (486), inline heater (414) heats concentrated disinfectant (92) to a temperature suitable to adequately decontaminate internal channels (420) as it will be apparent to those of ordinary skill in the art in view of the teachings herein. At step (488), as concentrated disinfectant (92) is transferred from disinfectant storage (411) to endoscope (400), flow sensor (416) measures the volume of disinfectant (92) delivered. Control system (20) ceases operation of disinfectant pump (412) when the volume of concentrated disinfectant (92) delivered to internal channel (420) is substantially equal to the capacity of internal channel (420), as seen at step (490). Subsequently, at step (492), flow sensor (416) closes the first flush valve (424) since internal channel (420) contains a sufficient amount of concentrated disinfectant (92) therein.

In the present example, at step (494), reprocessing system (410) determines whether a subsequent, contaminated channel (420) remains in system (410). With additional channels (420) connected to reprocessing system (410), a subsequent flush valve (424) is opened at step (496) and reprocessing system (410) reperforms steps (484) to step (496) until no subsequent, contaminated channel (420) remain in system (410). In this instance, as seen at step (497), reprocessing system (410) evaluates whether internal channels (420) have held concentrated disinfectant (92) for a minimum dwell time. As merely an illustrative example, the predetermined dwell time can range between approximately 10 seconds to 30 minutes.

At step (498), once reprocessing system (410) has determined that internal channels (420) has maintained concentrated disinfectant (92) therein for the minimum dwell time, concentrated disinfectant (92) is released from within internal channels (420) into basin (14a). For example, concentrated disinfectant (92) may be released or pushed out from internal channels (420) by flushing air or water through internal channels (420). In this instance, flush valves (424) remain open to allow the air or water to pass through flush lines (422) and into internal channels (420). In some versions, concentrated disinfectant (92) contained in internal channels (420) is released simultaneously. In some other versions, concentrated disinfectant (92) is released from internal channels (420) in a sequence (i.e., channel-by-channel). Other various suitable ways to release concentrated disinfectant (92) from internal channels (420) will be apparent to those of ordinary skill in the art in view of the teachings herein. Simultaneous with the release of concentrated disinfectant (92) into basin (14a) is the delivery of water from water source (50) into basin (14a). At step (499), reprocessing system (410) circulates the mixture of concentrated disinfectant (92) with the water in basin (14a) to thereby expose the outer surface of endoscope (400) to the lower concentrated solution of disinfectant (92). Reprocessing system (410) continues to circulate the mixture until a predetermined time elapses.

Figure 9:
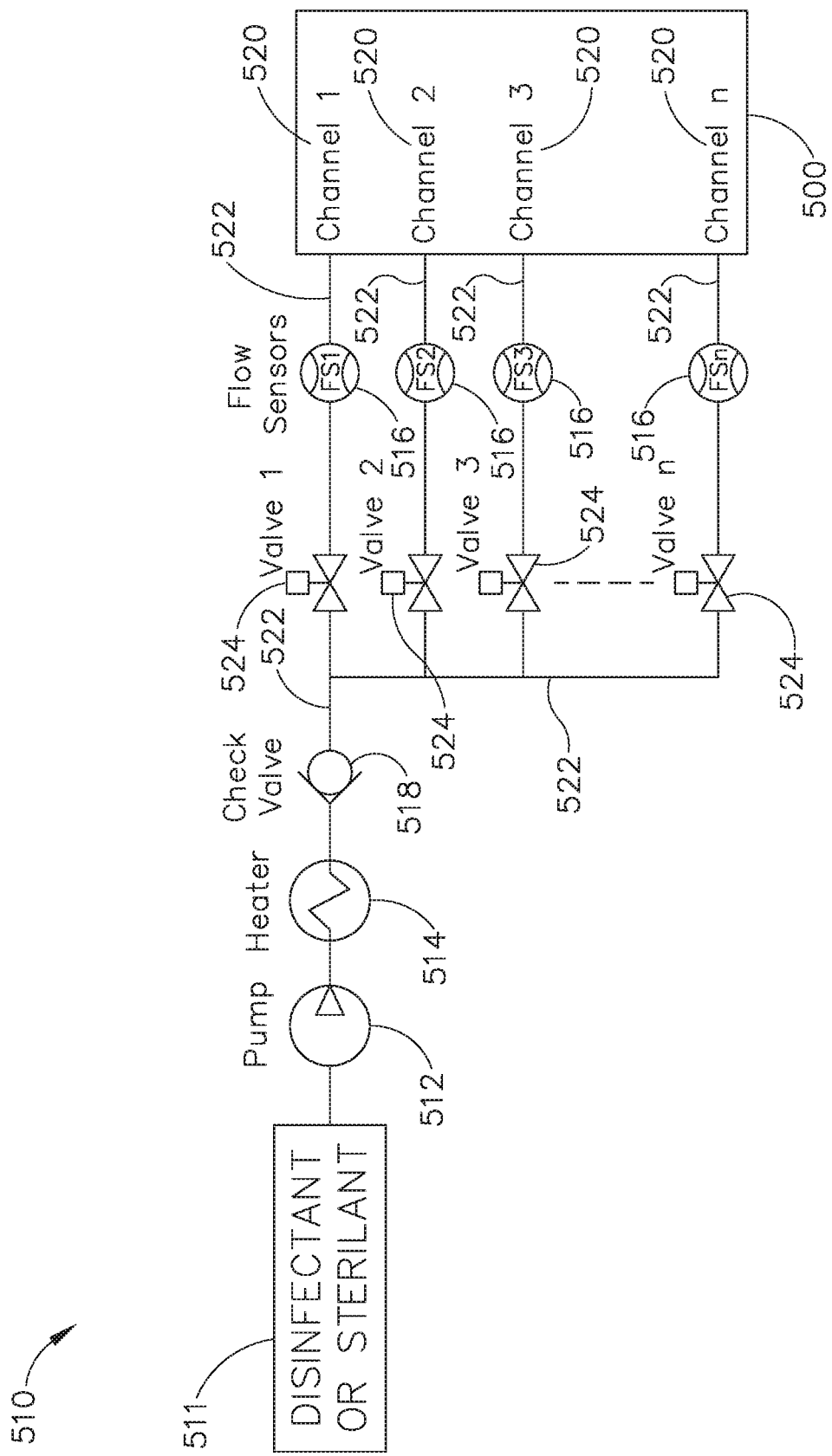
FIG. 9 depicts a partial schematic diagram of an exemplary variation of the reprocessing system of FIG. 1, including a respective flow sensor monitoring each endoscope channel.

FIG. 9 shows a block schematic of an exemplary alternative reprocessing system (510) including a disinfectant storage (511), a disinfectant pump (512), an inline heater (514), and a check valve (518). Except as otherwise described below, reprocessing system (510), disinfectant storage (511), disinfectant pump (512), inline heater (514), and check valve (518) are configured and operable just like reprocessing system (2, 310, 310'), disinfectant storage (92, 360), disinfectant pump (94), inline heater (80), and check valve (330), respectively, described above. Several internal channels (520) of an endoscope (500) are in fluid communication with disinfectant storage (511) via flush lines (522). Flush lines (522) include one or more flush valves (524) in line downstream of check valve (518) for each channel (520) operatively connected in reprocessing system (510). Unlike reprocessing system (410), reprocessing system (510) includes a respective flow sensor (516) for each channel (520) operatively connected to reprocessing system (510).

Reprocessing system (510) is operable to simultaneously deliver concentrated disinfectant (92) to internal channels (520) since reprocessing system (510) includes multiple flow sensors (516) to monitor the flow of concentrated disinfectant (92) delivered to the multiple channels (520). Each flow sensor (516) is downstream of flush valve (524) and is operable to monitor and measure the quantity of concentrated disinfectant (92) delivered from disinfectant pump (512) to the respective internal channels (520) of endoscope (500). Control system (20) is configured to open the flush valve (524) that is directly upstream and in fluid connection with the particular channel (520). Each flow sensor (516) is configured to identify the volume of internal channel (520) and to measure an amount of concentrated disinfectant (92) delivered to the channel (520). Reprocessing system (510) is configured to analyze the data measured by flow sensor (516) until the amount of concentrated disinfectant (92) delivered substantially fills the capacity of internal channels (520). In this instance, reprocessing system (510) is configured to individually close a respective flush valve (524) once the respective flow sensor (516) has determined that sufficient disinfectant solution (92) has been transferred to that particular internal channels (520).

In contrast to reprocessing system (410) described above, which only includes one flow sensor (416), reprocessing system (510) of the present example includes multiple flow sensors (516) such that each flow sensor (516) is configured to monitor a respective filling progress of an individual channel (520). In this instance, reprocessing system (510) is operable to fill all internal channels (520) with concentrated disinfectant (92) simultaneously, with each flow sensor (516) transmitting data to reprocessing system (510) on the amount of concentrated disinfectant (92) delivered. In the present example, reprocessing system (510) is able to cease delivery of concentrated disinfectant (92) to internal channels (520) when the respective capacity of each internal channel (520) has been substantially filled. With respect to reprocessing system (410), internal channels (420) are filled individually and sequentially as only a single flow sensor (416) is included and operable to monitor the delivery of concentrated disinfectant (92) to internal channel (420). While only one endoscope (500) is shown as being reprocessed in reprocessing system (510), it should be understood that reprocessing system (510) may be capable of reprocessing more than one endoscope (500) simultaneously and/or in a sequence.

Figure 10:
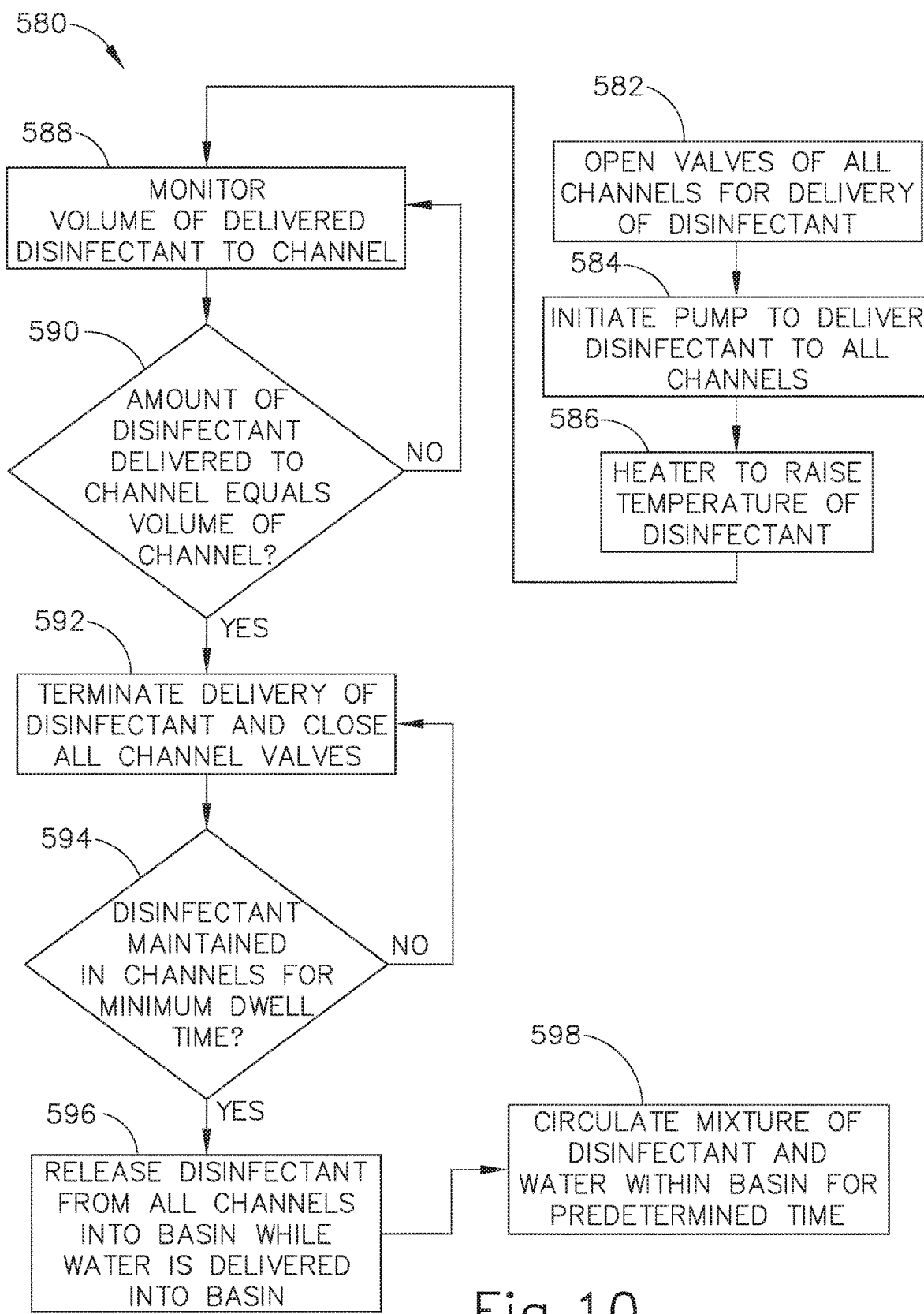
FIG. 10 depicts a flow diagram illustrating another exemplary reprocessing method utilized by the reprocessing system of FIG. 9, with a respective flow sensor monitoring the volume of disinfectant delivered to a particular channel of an endoscope.

FIG. 10 shows a flow diagram illustrating steps of an exemplary reprocessing method (580) that may be used by reprocessing system (510) to perform a disinfection cycle of internal channels (520) and the outer surface of endoscope (500). Once the desired number of rinsing and drying cycles have been completed, reprocessing system (510) opens all flush valves (524) in fluid connection with endoscope (500) through flush lines (522), as seen at step (582). At step (584), disinfectant pump (512) delivers concentrated disinfectant (92) to internal channels (520) of endoscope (500). In this instance, as seen at step (586), inline heater (514) heats concentrated disinfectant (92) to a temperature suitable to adequately decontaminate internal channels (520) of endoscope (500) as it will be apparent to those of ordinary skill in the art in view of the teachings herein.

At step (588), as concentrated disinfectant (92) is transferred from disinfectant storage (511) to internal channels (520), each flow sensor (516) measures the volume of disinfectant (92) delivered to the respective endoscope (500). With this data being transmitted from flow sensors (516), control system (20) is able to close flush valve (524) when the volume delivered to the respective channel (520) is substantially equal to the capacity of that channel (520), as seen at step (590). Subsequently, at step (592), reprocessing system (510) terminates the operation of disinfectant pump (512) and closes the last flush valve (524) that is in fluid communication with the last channel (520) that has received its capacity of concentrated disinfectant (92).

In the present example, at step (594), reprocessing system (510) evaluates whether internal channels (520) have held concentrated disinfectant (92) for the minimum dwell time. At step (596), once reprocessing system (510) has determined that internal channels (520) of a particular endoscope (500) have maintained concentrated disinfectant (92) therein for the minimum dwell time, concentrated disinfectant (92) is released from within internal channels (520) into basin (14a). For example, concentrated disinfectant (92) may be released or pushed out from internal channels (520) by flushing air or water through internal channels (520). In the instance where internal channels (520) are flushed out with water or air, flush valves (524) are opened to thereby allow the substance to pass through internal channels (520). It should be understood that concentrated disinfectant (92) may be released from all channels (520) simultaneously or in a sequential order. Other various suitable ways to release concentrated disinfectant (92) from internal channels (520) will be apparent to those of ordinary skill in the art in view of the teachings herein. Simultaneous with the release of concentrated disinfectant (92) into basin (14a) is the delivery of water from water source (50) into basin (14a). At step (598), once all internal channels (520) have been emptied of concentrated disinfectant (92), reprocessing system (510) circulates the mixture of concentrated disinfectant (92) with the water in basin (14a) to thereby expose the outer surfaces of endoscope (500) to the lower concentrated solution of disinfectant (92). Similar to reprocessing method (480), reprocessing system (510) continues to circulate the mixture until a predetermined time elapses.

Figure 11:
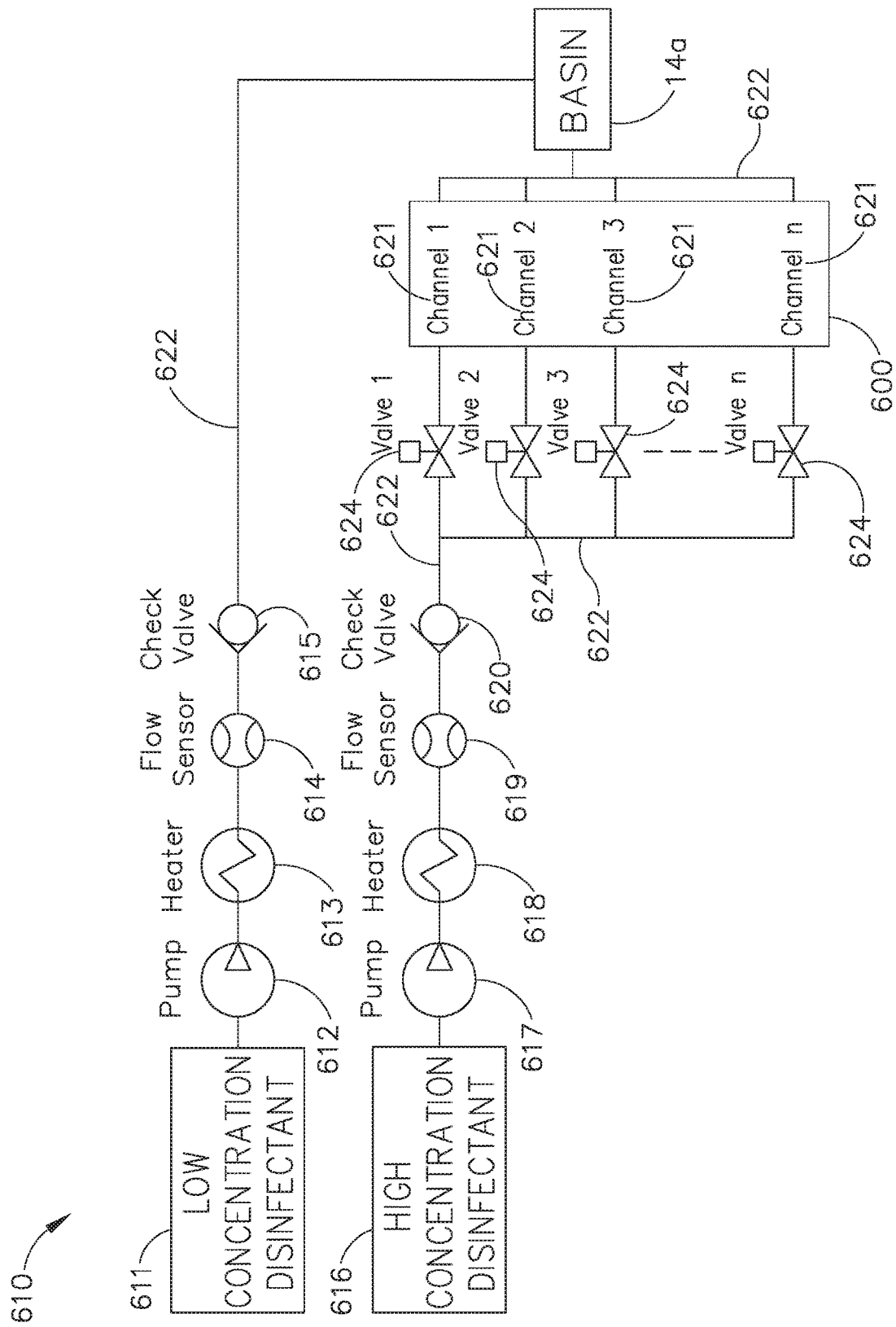
FIG. 11 depicts a partial schematic diagram of an exemplary variation of the reprocessing system of FIG. 1, including separate sources of high concentration disinfectant and low concentration disinfectant.

V. Exemplary Medical Device Reprocessing Apparatus and Method with Dedicated Concentration Channels FIG. 11 shows a block schematic of an exemplary reprocessing system (610) including a low concentration disinfectant storage (611) and a high concentration disinfectant storage (616). Low concentration disinfectant storage (611) is in fluid communication with a first disinfectant pump (612), a first inline heater (613), a first flow sensor (614) and a first check valve (615). Similarly, high concentration disinfectant storage (616) is in fluid communication with a second disinfectant pump (617), a second inline heater (618), a second flow sensor (619) and a second check valve (620). Except as otherwise described below, reprocessing system (610), disinfectant storages (511, 516), disinfectant pumps (512, 617), inline heaters (613, 618), flow sensors (614, 619) and check valves (615, 620) are configured and operable just like reprocessing system (2, 310, 310'), disinfectant storage (92), disinfectant pump (94), inline heater (80), and check valve (330), respectively, described above. Several channels (621) of an endoscope (600) are in fluid communication with high concentration disinfectant storage (616) via flush lines (622). Flush lines (622) include one or more flush valves (624) in line downstream of second check valve (620) for each channel (621) operatively connected to reprocessing system (610).

Reprocessing system (610) is operable to individually deliver high concentration disinfectant (92) to internal channels (621) of endoscope (600), similar to reprocessing system (410). In particular, second flow sensor (619) is operable to monitor and measure the quantity of high concentration disinfectant (92) delivered from second disinfectant pump (417) to internal channels (621). In other words, control system (20) is configured to open a particular flush valve (624) that is in fluid connection with a first channel (621), to identify the volume of that channel (621), and to deliver a corresponding amount of high concentration disinfectant (92) to substantially fill the capacity of that particular channel (621). In this instance, reprocessing system (610) is configured to close the current flush valve (624) and open a subsequent flush valve (624) that is in fluid connection with a subsequent internal channel (621) that has not yet received high concentration disinfectant (92).

Reprocessing system (610) is further operable to deliver low concentration disinfectant (87) from low concentration disinfectant storage (611) to basin (14a), through flush lines (622) that are separate from those that are in fluid communication with high concentration disinfectant storage (616). In particular, first flow sensor (614) is operable to monitor and measure the quantity of low concentration disinfectant (87) delivered from first disinfectant pump (612) to basin (14a). Reprocessing system (610) is configured to transfer low concentration disinfectant (87) to basin (14a) and circulate disinfectant (87) in basin (14a) as reprocessing system (610) simultaneously delivers high concentration disinfectant (92) to internal channels (621). In this instance, reprocessing system (610) is operable to disinfect internal channels (621) and the outer surface of endoscope (600) simultaneously. While only one endoscope (600) is shown as being reprocessed in reprocessing system (610), it should be understood that reprocessing system (610) may be capable of reprocessing more than one endoscope (600) simultaneously and/or in a sequence.

Figure 12:
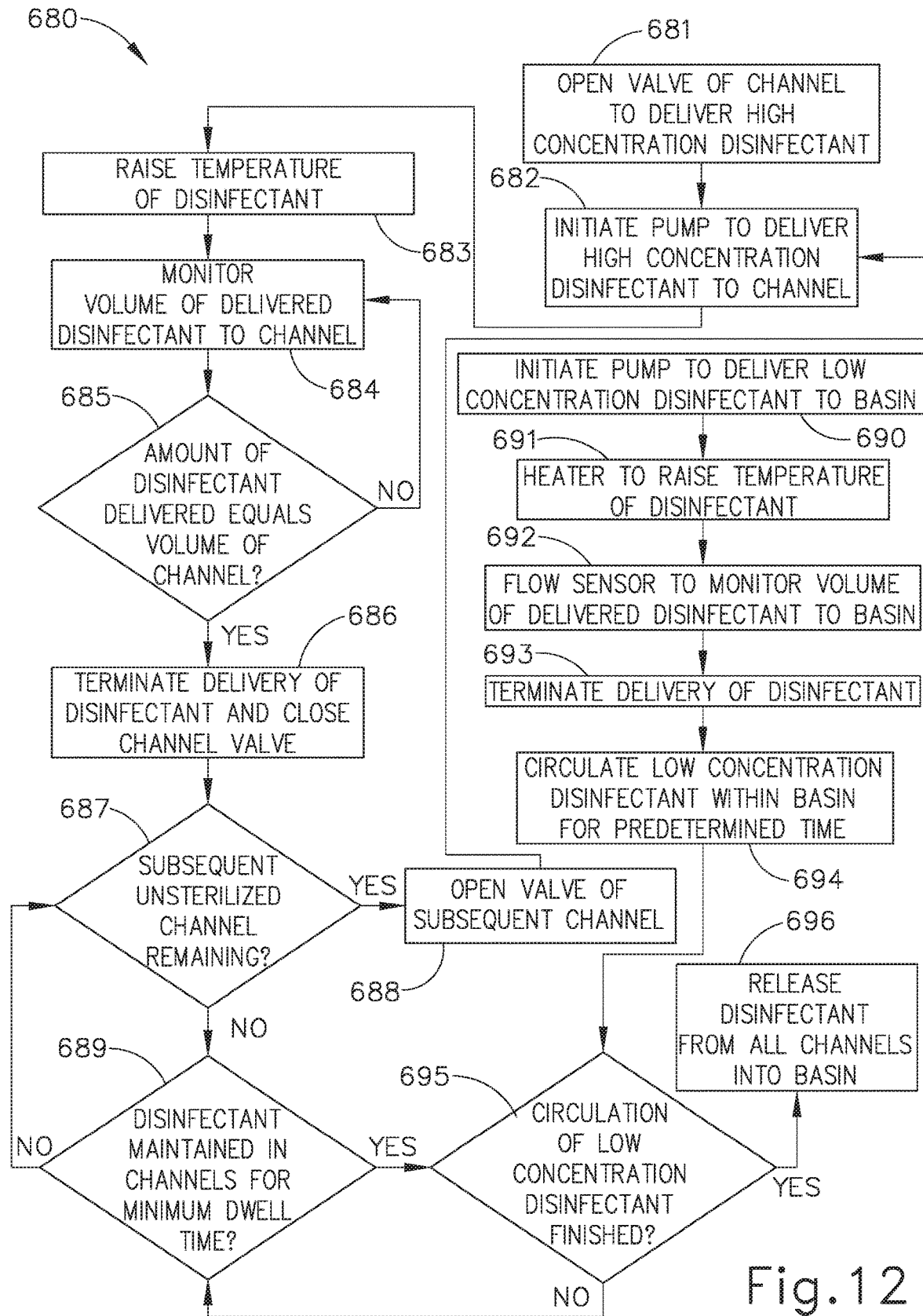
FIG. 12 depicts a flow diagram illustrating still another reprocessing method utilized by the reprocessing system of FIG. 11, with the high concentration disinfectant delivered to the internal channels of the endoscope and the low concentration disinfectant delivered to the external channels of the endoscope.

FIG. 12 shows a flow diagram illustrating steps of an exemplary reprocessing method (680) that may be used by reprocessing system (610) to perform a separate, yet simultaneous, disinfection cycle of internal channels (621) and external surface of endoscope (600). After reprocessing system (610) has completed the desired number of rinsing and drying cycles, first disinfectant pump (612) delivers low concentration disinfectant (87) to basin (14a), as seen at step (690). As will be discussed in greater detail below, reprocessing system (610) simultaneously opens a first flush valve (624) to separately deliver high concentration disinfectant (92) to internal channels (621) of endoscope (600), as seen in step (681).

At step (691), inline heater (613) heats low concentration disinfectant (87) to a temperature suitable to adequately decontaminate the outer surface of endoscope (600) as will be apparent to those of ordinary skill in the art in view of the teachings herein. At step (692), as low concentration disinfectant (87) is transferred from low concentration disinfectant storage (611) to basin (14a), first flow sensor (614) measures the volume of low concentration disinfectant (87) delivered. Reprocessing system (610) terminates the continued delivery of low concentration disinfectant (87) once an adequate amount of low concentration disinfectant (87) has been delivered to decontaminate the outer surface of endoscope (600). The adequate amount of disinfectant (87) to disinfect the outer surface of endoscope (600) will be apparent to those of ordinary skill in the art in view of the teachings herein. At step (693), with an adequate amount of low concentration disinfectant (87) delivered to basin (14a), reprocessing system (610) circulates low concentration disinfectant (87) within basin (14a) for a predetermined time to effectively disinfect the outer surface of endoscope (600). As seen at step (694), reprocessing system (610) continues to circulate low concentration disinfectant (87) in basin (14a) until the predetermined time has concluded.

As mentioned above, at step (681) reprocessing system (610) opens a first flush valve (624) in fluid connection with a first channel (621) through flush lines (622). At step (682), second disinfectant pump (617) delivers concentrated disinfectant (92) to the first channel (621). In this instance, as seen at step (683), inline heater (618) heats high concentration disinfectant (92) to a temperature suitable to adequately decontaminate internal channel (621) of endoscope (600) as will be apparent to those of ordinary skill in the art in view of the teachings herein. At step (684), as high concentration disinfectant (92) is transferred from high concentration disinfectant storage (616) to channels (621), second flow sensor (619) measures the volume of high concentration disinfectant (92) delivered. Reprocessing system (610) ceases operation of second disinfectant pump (617) when the volume delivered is substantially equal to the capacity of internal channels (621), as seen at step (685). Subsequently, at step (686), control system (20) closes the first flush valve (624) since the first internal channel (621) contains a sufficient amount of concentrated disinfectant (92) therein.

In the present example, at step (687), reprocessing system (610) determines whether a subsequent, contaminated internal channel (621) remains in system (610). With additional channels (621) connected to reprocessing system (610), a subsequent flush valve (624) is opened at step (688) and reprocessing system (610) reperforms steps (682) to step (687) until no subsequent, contaminated channel (621) remain in system (610). In this instance, as seen at step (689), reprocessing system (610) evaluates whether internal channels (621) have held high concentration disinfectant (92) for a minimum dwell time. As merely an illustrative example, the predetermined dwell time can range between approximately 10 seconds to 30 minutes.

At step (695), once reprocessing system (610) has determined that internal channels (621) have maintained high concentration disinfectant (92) therein for the minimum dwell time, reprocessing system (610) evaluates whether the circulation of low concentration (87) in basin (14a) has concluded. High concentration disinfectant (92) is not released into basin (14a) until step (695) has concluded. Once the outer surface of endoscope (600) has been fully disinfected via step (695), reprocessing system (610) proceeds to release high concentration disinfectant (92) from within internal channels (621) into basin (14a), as seen in step (696). For example, concentrated disinfectant (92) may be released or pushed out from internal channels (621) by flushing air or water through internal channels (621). As previously indicated, flush valves (624) will remain open in this instance where air, water, or some other substance is pushed through internal channels (621) to thereby flush concentrated disinfectant (92) out. Other various suitable ways to release concentrated disinfectant (92) from internal channels (621) will be apparent to those of ordinary skill in the art in view of the teachings herein.

Although not shown, it should be understood that reprocessing method (680) may be integrated with reprocessing system (310, 310', 510) such that separate delivery channels are provided for high concentration disinfectant (92) and low-contaminate disinfectant (87) with flow sensors (619) provided for each endoscope (600). In this instance, high concentration disinfectant (92) is delivered from high concentration disinfectant storage (616) to multiple internal channels (621) simultaneously, rather than sequentially through a single flow sensor (619) as shown in FIG. 11. Additionally, it should be understood that reprocessing systems (410, 510, 610) may have multiple endoscopes (400, 500, 600) connected therein such that reprocessing methods (480, 580, 680) are repeated for each endoscope (400, 500, 600), respectively.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A medical device processor comprising: (a) an enclosure for holding at least one medical device, wherein the at least one medical device comprises an outer surface and at least one internal channel; (b) a first reservoir, wherein the first reservoir includes a disinfectant contained therein; (c) a water source, wherein the water source includes water contained therein; (d) a mixing chamber in fluid communication with the water source; and (e) a liquid distribution system in fluid communication with the first reservoir and configured to deliver the disinfectant from the first reservoir to the at least one medical device, wherein the liquid distribution system is in fluid communication with the water source and is configured to deliver the water from the water source to the mixing chamber, the liquid distribution system comprising: (i) a pump, wherein the pump is operable to deliver the disinfectant from the first reservoir to the at least one internal channel of the at least one medical device, and (ii) a flow sensor, wherein the flow sensor is operable to monitor the disinfectant delivered by the pump to the at least one internal channel of the at least one medical device; wherein the liquid distribution system is further configured to release the disinfectant from the at least one internal channel into the mixing chamber to mix with water from the water source to thereby disinfect the outer surface of the at least one medical device.

Example 2

The medical device processor of Example 1, wherein the disinfectant contained within the first reservoir is a concentrated disinfectant, wherein the liquid distribution system is configured to deliver the concentrated disinfectant to the at least one internal channel while preventing the outer surface from being exposed to the concentrated disinfectant.

Example 3

The medical device processor of any one or more of Example 2, wherein the medical device comprises a plurality of internal channels, wherein the liquid distribution system is configured to fill the internal channels of the at least one medical device with the concentrated disinfectant in a sequence.

Example 4

The medical device processor of any one or more of Examples 1 through 3, wherein the liquid distribution system is operable to identify other internal channels of the at least one medical device that have not received the concentrated disinfectant.

Example 5

The medical device processor of any one or more of Examples 2 through 4, wherein the liquid distribution system is configured to measure an elapsed duration that at least one internal channel has held the concentrated disinfectant.

Example 6

The medical device processor of Example 5, wherein the liquid distribution system is configured to release the concentrated disinfectant from the at least one internal channel into the mixing chamber when the elapsed duration reaches a predetermined dwell time.

Example 7

The medical device processor of any one or more of Examples 2 through 6, wherein the liquid distribution system is configured to release the concentrated disinfectant from the at least one internal channel into the mixing chamber when the elapsed duration reaches a predetermined dwell time.

Example 8

The medical device processor of any one or more of Examples 2 through 7, wherein the liquid distribution system is configured to release water from the water source into the mixing chamber simultaneously with the release of the concentrated disinfectant from the at least one internal channel into the mixing chamber.

Example 9

The medical device processor of any one or more of Examples 2 through 8, wherein the mixing chamber is operable to circulate and mix the water and the concentrated disinfectant to thereby form a solution such that the outer surface of the at least one medical device is exposed to the solution.

Example 10

The medical device processor of any one or more of Examples 1 through 9, wherein the liquid distribution system is configured to monitor a volume of the disinfectant delivered to the at least one internal channel of the at least one medical device such that the liquid distribution system is configured to cease operation of the pump when the volume delivered substantially equals a capacity of the at least one internal channel 1.

Example 11

The medical device processor of Example 10, further comprising at least one flow sensor for each of the at least one internal channel of the at least one medical device, wherein the at least one flow sensor is configured to measure the volume of the disinfectant delivered to the at least one internal channel.

Example 12

The medical device processor of any one or more of Examples 1 through 11, further comprising a second reservoir, wherein the second reservoir contains a diluted disinfectant contained therein, wherein the disinfectant in the first reservoir is a concentrated disinfectant.

Example 13

The medical device processor of Example 12, wherein the second reservoir is in fluid communication with a second pump and a second flow sensor.

Example 14

The medical device processor of Example 12 through Example 13, wherein the liquid distribution system is configured to deliver the diluted disinfectant to the mixing chamber to thereby expose the outer surface of the at least one medical device to the diluted disinfectant.

Example 15

The medical device processor of Example 14, wherein the liquid distribution system is configured to deliver the concentrated disinfectant to the at least one internal channel of the at least one medical device simultaneous with the delivery of the diluted disinfectant to the mixing chamber.

Example 16

A method for reprocessing at least one medical device contained within an enclosure, the enclosure comprising a liquid distribution system in fluid communication with a mixing chamber, wherein the at least one medical device is held within the mixing chamber, the method comprising: (a) activating a pump to deliver a disinfectant or detergent to an internal channel of the at least one medical device; (b) deactivating the pump and closing a valve in fluid communication with the internal channel once a time threshold is achieved; (c) releasing the disinfectant or detergent from the internal channel and into the mixing chamber when the internal channel has held the disinfectant or detergent for a minimum dwell time; (d) activating a pump to deliver water to the mixing chamber; and (e) circulating the mixture of the disinfectant or detergent and the water in the mixing chamber for a predetermined time thereby exposing an outer surface of the at least one medical device to the mixture.

Example 17

The method of reprocessing at least one medical device of Example 16, further comprising heating the disinfectant or detergent with an inline heater as the disinfectant or detergent is being pumped from the first reservoir to the internal channels of the at least one medical device.

Example 18

The method of reprocessing at least one medical device of any one or more of Examples 16 through 17, further comprising (a) activating a second pump to deliver a diluted disinfectant or detergent to the mixing chamber; and (b) circulating the diluted disinfectant or detergent in the mixing chamber for a predetermined time thereby exposing an outer surface of the at least one medical device to the diluted disinfectant or detergent.

Example 19

The method of reprocessing at least one medical device of any one or more of Examples 16 through 18, further comprising opening a subsequent valve in fluid communication with a subsequent internal channel of the at least one medical device and repeating steps (a) through (c).

Example 20

A method for reprocessing at least one medical device contained within an enclosure, the at least one medical device including an internal channel having a volume, the enclosure comprising a liquid distribution system in fluid communication with a mixing chamber, wherein the at least one medical device is held within the mixing chamber, the method comprising: (a) activating a pump to deliver a disinfectant or detergent to an internal channel of the at least one medical device; (b) deactivating the pump once an amount of the disinfectant or detergent delivered to the internal channel substantially equals the volume of the internal channel; (c) closing a valve in fluid communication with the internal channel; (d) releasing the disinfectant or detergent from the internal channel and into the mixing chamber when the internal channel has held the disinfectant or detergent for a minimum dwell time; (f) activating a pump to deliver water to the mixing chamber; and (g) circulating a mixture of the disinfectant or detergent and the water in the mixing chamber for a predetermined time thereby exposing an outer surface of the at least one medical device to the mixture.

VII. Miscellaneous

As noted above, while the teachings herein are provided in the context of delivering disinfectant to the outer surface and internal channels (210, 212, 213, 214, 217, 218) of endoscopes (200) and other similar instruments, the same teachings may be readily applied to delivery of detergent to the outer surface and internal channels (210, 212, 213, 214, 217, 218) of endoscopes (200) and other similar instruments.

In various examples described above, the high concentration disinfectant (or detergent) is held in channels (420, 520, 621) for a particular dwell time, before being released into basin (14a). In some other variations, rather than holding the high concentration disinfectant (or detergent) is held in channels (420, 520, 621) for a particular dwell time, the high concentration disinfectant (or detergent) may be circulated through channels (420, 520, 621) for a particular circulation time. In other words, the high concentration disinfectant (or detergent) may be in constant motion through channels (420, 520, 621) for a certain duration before being released into basin (14a). As another merely illustrative example, the high concentration disinfectant (or detergent) may be moved and held through and in channels (420, 520, 621) in a particular pattern (e.g., circulate for 5 seconds, then hold for 5 seconds, then circulate for 5 seconds, etc.) for a certain duration before being released into basin (14a). In either of these variations, the motion of the high concentration disinfectant (or detergent) through channels (420, 520, 621) may promote better contact and prevent voids within channels (420, 520, 621). Various suitable ways in which the teachings herein may be modified to provide constant or intermittent motion of high concentration disinfectant (or detergent) through channels (420, 520, 621), before the high concentration disinfectant (or detergent) is deposited in basin (14a), will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A medical device processor comprising:
   (a) an enclosure for holding at least one medical device, wherein the at least one medical device comprises an outer surface and at least one internal channel;
   (b) a first reservoir, wherein the first reservoir includes a concentrated disinfectant contained therein;
   (c) a water source;
   (d) a mixing chamber in fluid communication with the water source; and
   (e) a liquid distribution system in fluid communication with the first reservoir and configured to deliver the concentrated disinfectant from the first reservoir to the at least one internal channel of the at least one medical device to thereby disinfect the at least one channel, wherein the liquid distribution system is in fluid communication with the water source and is configured to deliver the water from the water source to the mixing chamber, the liquid distribution system comprising:
      (i) a pump, wherein the pump is configured to deliver the concentrated disinfectant from the first reservoir to the at least one internal channel of the at least one medical device, and
      (ii) a flow sensor, wherein the flow sensor is configured to monitor the concentrated disinfectant delivered by the pump to the at least one internal channel of the at least one medical device;
   wherein the liquid distribution system is further configured to release the concentrated disinfectant from the at least one internal channel into the mixing chamber to mix with water from the water source to thereby disinfect the outer surface of the at least one medical device, while preventing the outer surface from being exposed to the concentrated disinfectant prior to mixing with water from the water source.

2. The medical device processor of claim 1, wherein the medical device comprises a plurality of internal channels, wherein the liquid distribution system is configured to fill the internal channels of the at least one medical device with the concentrated disinfectant in a sequence.

3. The medical device processor of claim 2, wherein the liquid distribution system is operable to identify other internal channels of the at least one medical device that have not received the concentrated disinfectant.

4. The medical device processor of claim 1, wherein the liquid distribution system is configured to measure an elapsed duration that at least one internal channel has held the concentrated disinfectant.

5. The medical device processor of claim 4, wherein the liquid distribution system is configured to release the concentrated disinfectant from the at least one internal channel into the mixing chamber when the elapsed duration reaches a predetermined dwell time.

6. The medical device processor of claim 1, wherein the liquid distribution system is configured to release the concentrated disinfectant from the at least one internal channel into the mixing chamber when the elapsed duration reaches a predetermined dwell time.

7. The medical device processor of claim 1, wherein the liquid distribution system is configured to release water from the water source into the mixing chamber simultaneously with the release of the concentrated disinfectant from the at least one internal channel into the mixing chamber.

8. The medical device processor of claim 1, wherein the mixing chamber is operable to circulate and mix the water and the concentrated disinfectant to thereby form a solution such that the outer surface of the at least one medical device is exposed to the solution.

9. The medical device processor of claim 1, wherein the liquid distribution system is configured to monitor a volume of the disinfectant delivered to the at least one internal channel of the at least one medical device such that the liquid distribution system is configured to cease operation of the pump when the volume delivered substantially equals a capacity of the at least one internal channel.

10. The medical device processor of claim 9, further comprising at least one flow sensor for each of the at least one internal channel of the at least one medical device, wherein the at least one flow sensor is configured to measure the volume of the disinfectant delivered to the at least one internal channel.

11. The medical device processor of claim 1, further comprising a second reservoir, wherein the second reservoir contains a diluted disinfectant contained therein.

12. The medical device processor of claim 11, wherein the second reservoir is in fluid communication with a second pump and a second flow sensor.

13. The medical device processor of claim 12, wherein the liquid distribution system is configured to deliver the diluted disinfectant to the mixing chamber to thereby expose the outer surface of the at least one medical device to the diluted disinfectant.

14. The medical device processor of claim 13, wherein the liquid distribution system is configured to deliver the concentrated disinfectant to the at least one internal channel of the at least one medical device simultaneous with the delivery of the diluted disinfectant to the mixing chamber.

* * * * *